(12) United States Patent
Sather et al.

(10) Patent No.: US 8,875,711 B2
(45) Date of Patent: Nov. 4, 2014

(54) LAYERED NASAL RESPIRATORY DEVICES

(75) Inventors: Elliot Sather, San Francisco, CA (US);
Arthur Ferdinand, San Jose, CA (US);
Michael L. Favet, San Jose, CA (US);
Danny Yu-Youh Lai, San Jose, CA
(US); Rajiv Doshi, Los Altos, CA (US)

(73) Assignee: Theravent, Inc., San Jose, CA (US)

( * ) Notice: Subject to any disclaimer, the term of this patent is extended or adjusted under 35 U.S.C. 154(b) by 399 days.

(21) Appl. No.: 13/117,933

(22) Filed: May 27, 2011

(65) Prior Publication Data

US 2011/0290256 A1 Dec. 1, 2011

Related U.S. Application Data

(60) Provisional application No. 61/349,139, filed on May 27, 2010, provisional application No. 61/361,275, filed on Jul. 2, 2010.

(51) Int. Cl.
| | | |
|---|---|---|
| *A61M 11/00* | (2006.01) | |
| *A61M 16/08* | (2006.01) | |
| *A61M 16/20* | (2006.01) | |
| *A61F 5/08* | (2006.01) | |
| *A61M 16/06* | (2006.01) | |
| *A61F 5/56* | (2006.01) | |

(52) U.S. Cl.
CPC ..... *A61M 16/208* (2013.01); *A61M 2210/0618* (2013.01); *A61M 16/0866* (2014.02); *A61F 5/08* (2013.01); *A61M 16/0688* (2014.02); *A61F 5/56* (2013.01)
USPC .................................................. 128/207.18

(58) Field of Classification Search
USPC ............ 128/206.11, 204.12, 204.11, 207.18, 128/206.18, 206.15
See application file for complete search history.

(56) References Cited

U.S. PATENT DOCUMENTS

| | | |
|---|---|---|
| 69,396 A | 10/1867 | Curtis |
| 628,111 A | 7/1899 | McHatton |
| 669,098 A | 3/1901 | Overshiner |
| 675,275 A | 5/1901 | Gunning |
| 718,785 A | 1/1903 | McNary |

(Continued)

FOREIGN PATENT DOCUMENTS

| | | |
|---|---|---|
| EP | 0434258 A2 | 6/1991 |
| EP | 1157663 A1 | 11/2001 |

(Continued)

OTHER PUBLICATIONS

Doshi et al.; U.S. Appl. No. 13/212,948 entitled "Packaging and dispensing nasal devices," filed Aug. 18, 2011.

(Continued)

*Primary Examiner* — Steven Douglas
(74) *Attorney, Agent, or Firm* — Shay Glenn LLP

(57) ABSTRACT

Described herein are nasal devices, including nasal devices formed in layers having four or fewer layers. In some variations, the nasal devices include a single integrated layer from which the flap of the airflow resistor is formed as well as the base of the holdfast region. The nasal devices may include a single aligner or rim body on the side of the device facing the subject. The aligner may protect the airflow resistor, and may help center or position the nasal device. In some variations, these nasal devices may include a noise-reduction feature. Also described herein are systems, devices and methods for determining if a passive nasal respiratory device having an airflow resistor configured to inhibit exhalation more than inhalation has been worn by a subject, and thereby confirming compliance.

15 Claims, 29 Drawing Sheets

(56) References Cited

U.S. PATENT DOCUMENTS

| | | |
|---|---|---|
| 746,869 A | 12/1903 | Moulton |
| 774,446 A | 11/1904 | Moulton |
| 810,617 A | 1/1906 | Carence |
| 1,819,884 A | 8/1931 | Fores |
| 2,198,959 A | 4/1940 | Clarke |
| 2,237,954 A | 4/1941 | Wilson |
| 2,264,153 A | 11/1941 | Rowe |
| 2,274,886 A | 3/1942 | Carroll |
| 2,282,681 A | 5/1942 | Stotz |
| 2,335,936 A | 12/1943 | Hanlon |
| 2,433,565 A | 12/1947 | Korman |
| 2,448,724 A | 9/1948 | McGovney |
| 2,593,315 A | 4/1952 | Kraft |
| 2,672,138 A | 3/1954 | Carlock |
| 2,751,906 A | 6/1956 | Irvine |
| 2,777,442 A | 1/1957 | Zelano |
| 3,145,711 A | 8/1964 | Beber |
| 3,315,701 A | 4/1967 | Stilwell |
| 3,370,305 A | 2/1968 | Goott et al. |
| 3,451,392 A | 6/1969 | Cook et al. |
| 3,463,149 A | 8/1969 | Albu |
| 3,513,839 A | 5/1970 | Vacante |
| 3,556,122 A | 1/1971 | Laerdal |
| 3,616,802 A | 11/1971 | Marinaccio |
| 3,657,855 A | 4/1972 | Swezey |
| 3,695,265 A | 10/1972 | Brevik |
| 3,710,799 A | 1/1973 | Caballero |
| 3,722,509 A | 3/1973 | Nebel |
| 3,747,597 A | 7/1973 | Olivera |
| 3,802,426 A | 4/1974 | Sakamoto |
| 3,884,223 A | 5/1975 | Keindl |
| 3,902,621 A | 9/1975 | Hidding |
| 4,004,584 A | 1/1977 | Geaney |
| 4,030,491 A | 6/1977 | Mattila |
| 4,040,428 A | 8/1977 | Clifford |
| 4,054,134 A | 10/1977 | Kritzer |
| 4,062,358 A | 12/1977 | Kritzer |
| 4,094,316 A | 6/1978 | Nathanson |
| 4,143,872 A | 3/1979 | Havstad et al. |
| 4,212,296 A | 7/1980 | Schaar |
| 4,220,150 A | 9/1980 | King |
| 4,221,217 A | 9/1980 | Amezcua |
| 4,226,233 A | 10/1980 | Kritzer |
| 4,240,420 A | 12/1980 | Riaboy |
| 4,267,831 A | 5/1981 | Aguilar |
| 4,325,366 A | 4/1982 | Tabor |
| 4,327,719 A | 5/1982 | Childers |
| RE31,040 E | 9/1982 | Possis |
| 4,354,489 A | 10/1982 | Riaboy |
| 4,403,616 A | 9/1983 | King |
| 4,456,016 A | 6/1984 | Nowacki et al. |
| 4,487,207 A | 12/1984 | Fitz |
| 4,533,137 A | 8/1985 | Sonne |
| 4,582,058 A | 4/1986 | Depel et al. |
| 4,584,997 A | 4/1986 | Delong |
| 4,601,465 A | 7/1986 | Roy |
| 4,640,277 A | 2/1987 | Meyer et al. |
| 4,651,873 A | 3/1987 | Stolcenberg et al. |
| 4,702,374 A | 10/1987 | Kelner |
| 4,718,554 A | 1/1988 | Barbato |
| 4,739,987 A | 4/1988 | Nicholson |
| 4,759,356 A | 7/1988 | Muir |
| 4,822,354 A | 4/1989 | Elosegui |
| 4,854,574 A | 8/1989 | Larson et al. |
| 4,860,766 A | 8/1989 | Sackner |
| 4,862,903 A | 9/1989 | Campbell |
| 4,908,028 A | 3/1990 | Colon et al. |
| 4,913,138 A | 4/1990 | Yoshida et al. |
| 4,919,138 A | 4/1990 | Nordenstroom |
| 4,973,047 A | 11/1990 | Norell |
| 4,979,505 A | 12/1990 | Cox |
| 4,984,302 A | 1/1991 | Lincoln |
| 4,984,581 A | 1/1991 | Stice |
| 5,016,425 A | 5/1991 | Weick |
| 5,033,312 A | 7/1991 | Stupecky |
| 5,038,621 A | 8/1991 | Stupecky |
| 5,052,400 A | 10/1991 | Dietz |
| 5,059,208 A | 10/1991 | Coe et al. |
| 5,074,293 A | 12/1991 | Lott et al. |
| 5,078,739 A | 1/1992 | Martin |
| 5,092,781 A | 3/1992 | Casciotti et al. |
| 5,117,820 A | 6/1992 | Robitaille |
| 5,197,980 A | 3/1993 | Gorshkov et al. |
| 5,255,687 A | 10/1993 | McKenna |
| 5,383,470 A | 1/1995 | Kolbly |
| 5,385,542 A | 1/1995 | Rawlings |
| 5,391,205 A | 2/1995 | Knight |
| 5,392,773 A | 2/1995 | Bertrand |
| 5,394,867 A | 3/1995 | Swann |
| 5,414,627 A | 5/1995 | Wada et al. |
| 5,415,660 A | 5/1995 | Campbell et al. |
| 5,425,359 A | 6/1995 | Liou |
| 5,459,544 A | 10/1995 | Emura |
| 5,522,382 A | 6/1996 | Sullivan et al. |
| 5,535,739 A | 7/1996 | Rapoport et al. |
| 5,562,641 A | 10/1996 | Flomenblit et al. |
| 5,568,808 A | 10/1996 | Rimkus |
| 5,572,994 A | 11/1996 | Smith |
| 5,607,469 A | 3/1997 | Frey |
| 5,649,533 A | 7/1997 | Oren |
| 5,665,104 A | 9/1997 | Lee |
| 5,727,546 A | 3/1998 | Clarke et al. |
| 5,730,122 A | 3/1998 | Lurie |
| 5,740,798 A | 4/1998 | McKinney |
| 5,743,256 A | 4/1998 | Jalowayski |
| 5,763,979 A | 6/1998 | Mukherjee et al. |
| 5,775,335 A | 7/1998 | Seal |
| 5,782,896 A | 7/1998 | Chen et al. |
| 5,797,920 A | 8/1998 | Kim |
| 5,803,121 A | 9/1998 | Estes |
| 5,823,187 A | 10/1998 | Estes et al. |
| 5,848,590 A | 12/1998 | Smith |
| 5,865,170 A | 2/1999 | Moles |
| 5,876,434 A | 3/1999 | Flomenblit et al. |
| 5,890,998 A | 4/1999 | Hougen |
| 5,899,832 A | 5/1999 | Hougen |
| 5,910,071 A | 6/1999 | Hougen |
| 5,911,756 A | 6/1999 | Debry |
| 5,947,119 A | 9/1999 | Reznick |
| 5,954,766 A | 9/1999 | Zadno-Azizi et al. |
| 5,957,978 A | 9/1999 | Blom |
| 5,992,006 A | 11/1999 | Datsikas |
| 6,004,342 A | 12/1999 | Filis |
| 6,058,932 A | 5/2000 | Hughes |
| 6,083,141 A | 7/2000 | Hougen |
| D430,667 S | 9/2000 | Rome |
| 6,119,690 A | 9/2000 | Pantaleo |
| 6,165,133 A | 12/2000 | Rapoport et al. |
| 6,177,482 B1 | 1/2001 | Cinelli et al. |
| 6,189,532 B1 | 2/2001 | Hely et al. |
| 6,213,955 B1 | 4/2001 | Karakasoglu et al. |
| 6,219,997 B1 | 4/2001 | Friberg et al. |
| 6,258,100 B1 | 7/2001 | Alferness et al. |
| 6,287,290 B1 | 9/2001 | Perkins et al. |
| 6,293,951 B1 | 9/2001 | Alferness et al. |
| 6,311,839 B1 | 11/2001 | Lo |
| 6,328,038 B1 | 12/2001 | Kessler et al. |
| 6,369,126 B1 | 4/2002 | Cinelli et al. |
| 6,398,775 B1 | 6/2002 | Perkins et al. |
| 6,439,233 B1 | 8/2002 | Geertsema |
| 6,484,725 B1 | 11/2002 | Chi |
| 6,500,095 B1 | 12/2002 | Hougen |
| 6,510,846 B1 | 1/2003 | O'Rourke |
| 6,527,761 B1 | 3/2003 | Soltesz et al. |
| 6,561,188 B1 | 5/2003 | Ellis |
| 6,562,057 B2 | 5/2003 | Santin |
| 6,568,387 B2 | 5/2003 | Davenport et al. |
| 6,573,421 B1 | 6/2003 | Lemaire |
| 6,581,598 B1 | 6/2003 | Foran et al. |
| 6,585,639 B1 | 7/2003 | Kotmel et al. |
| 6,592,594 B2 | 7/2003 | Rimbaugh et al. |
| 6,592,995 B2 | 7/2003 | Topolkaraev et al. |
| 6,595,215 B2 | 7/2003 | Wood |
| 6,609,516 B2 | 8/2003 | Hollander et al. |

(56) References Cited

U.S. PATENT DOCUMENTS

| | | |
|---|---|---|
| 6,626,172 B1 | 9/2003 | Karow et al. |
| 6,626,179 B1 | 9/2003 | Pedley |
| 6,631,721 B1 | 10/2003 | Salter et al. |
| 6,679,264 B1 | 1/2004 | Deem et al. |
| 6,694,979 B2 | 2/2004 | Deem et al. |
| 6,722,360 B2 | 4/2004 | Doshi |
| 6,726,598 B1 | 4/2004 | Jarvis et al. |
| 6,737,160 B1 | 5/2004 | Full et al. |
| 6,769,432 B1 | 8/2004 | Keifer |
| 6,776,162 B2 | 8/2004 | Wood |
| 6,776,163 B2 | 8/2004 | Dougill et al. |
| 6,811,538 B2 | 11/2004 | Westbrook et al. |
| 6,841,716 B1 | 1/2005 | Tsutsumi |
| 6,848,446 B2 | 2/2005 | Noble |
| 6,863,066 B2 | 3/2005 | Ogle |
| 6,866,652 B2 | 3/2005 | Bierman |
| 6,872,439 B2 | 3/2005 | Fearing et al. |
| 6,913,017 B2 | 7/2005 | Roberts |
| 6,921,574 B2 | 7/2005 | Cinelli et al. |
| 6,997,177 B2 | 2/2006 | Wood |
| 7,011,723 B2 | 3/2006 | Full et al. |
| 7,013,896 B2 | 3/2006 | Schmidt |
| 7,047,969 B2 | 5/2006 | Noble |
| 7,156,098 B2 | 1/2007 | Dolezal et al. |
| 7,175,723 B2 | 2/2007 | Jones et al. |
| 7,178,524 B2 | 2/2007 | Noble |
| 7,201,169 B2 | 4/2007 | Wilkie et al. |
| D542,407 S | 5/2007 | Stallard et al. |
| 7,263,996 B2 | 9/2007 | Yung Ho |
| 7,334,581 B2 | 2/2008 | Doshi |
| D566,834 S | 4/2008 | Barton |
| 7,422,014 B1 | 9/2008 | Smith |
| 7,506,649 B2 | 3/2009 | Doshi et al. |
| 7,559,326 B2 | 7/2009 | Smith et al. |
| 7,578,294 B2 | 8/2009 | Pierro et al. |
| 7,640,934 B2 | 1/2010 | Zollinger et al. |
| 7,735,491 B2 | 6/2010 | Doshi et al. |
| 7,735,492 B2 | 6/2010 | Doshi et al. |
| 7,798,148 B2 | 9/2010 | Doshi et al. |
| 7,806,120 B2 | 10/2010 | Loomas et al. |
| 7,856,979 B2 | 12/2010 | Doshi et al. |
| 7,880,051 B2 | 2/2011 | Madsen et al. |
| 7,987,852 B2 | 8/2011 | Doshi et al. |
| 7,992,563 B2 | 8/2011 | Doshi |
| 7,992,564 B2 | 8/2011 | Doshi et al. |
| 7,992,566 B2 | 8/2011 | Pflueger et al. |
| 8,020,700 B2 | 9/2011 | Doshi et al. |
| 8,061,357 B2 | 11/2011 | Pierce et al. |
| 2001/0051799 A1 | 12/2001 | Ingenito |
| 2001/0056274 A1 | 12/2001 | Perkins et al. |
| 2002/0062120 A1 | 5/2002 | Perkins et al. |
| 2002/0077593 A1 | 6/2002 | Perkins et al. |
| 2002/0112729 A1 | 8/2002 | DeVore et al. |
| 2002/0157673 A1 | 10/2002 | Kessler et al. |
| 2003/0024527 A1 | 2/2003 | Ginn |
| 2003/0050648 A1 | 3/2003 | Alferness et al. |
| 2003/0070682 A1 | 4/2003 | Wilson et al. |
| 2003/0106555 A1 | 6/2003 | Tovey |
| 2003/0106556 A1 | 6/2003 | Alperovich et al. |
| 2003/0140925 A1 | 7/2003 | Sapienza et al. |
| 2003/0149387 A1 | 8/2003 | Barakat et al. |
| 2003/0154988 A1 | 8/2003 | DeVore et al. |
| 2003/0158515 A1 | 8/2003 | Gonzalez et al. |
| 2003/0195552 A1 | 10/2003 | Santin |
| 2003/0209247 A1 | 11/2003 | O'Rourke |
| 2004/0016432 A1 | 1/2004 | Genger et al. |
| 2004/0020489 A1 | 2/2004 | Gillespie et al. |
| 2004/0020492 A1 | 2/2004 | Dubrul et al. |
| 2004/0020493 A1 | 2/2004 | Wood |
| 2004/0055606 A1 | 3/2004 | Hendricksen et al. |
| 2004/0112379 A1 | 6/2004 | Djupesland |
| 2004/0123868 A1 | 7/2004 | Rutter |
| 2004/0149615 A1 | 8/2004 | Eisenbraun |
| 2004/0254491 A1 | 12/2004 | Ricciardelli |
| 2004/0261791 A1 | 12/2004 | Horian |
| 2004/0261798 A1 | 12/2004 | Rimkus |
| 2005/0010125 A1 | 1/2005 | Joy et al. |
| 2005/0011524 A1 | 1/2005 | Thomlinson et al. |
| 2005/0033344 A1 | 2/2005 | Dillard et al. |
| 2005/0051170 A1 | 3/2005 | Koo |
| 2005/0066965 A1 | 3/2005 | Cronk et al. |
| 2005/0133039 A1 | 6/2005 | Wood |
| 2005/0211250 A1 | 9/2005 | Dolezal et al. |
| 2005/0279351 A1 | 12/2005 | Lewis et al. |
| 2005/0284479 A1 | 12/2005 | Schrader et al. |
| 2006/0000472 A1 | 1/2006 | Fenton |
| 2006/0016450 A1 | 1/2006 | Pearson et al. |
| 2006/0085027 A1 | 4/2006 | Santin et al. |
| 2006/0169285 A1 | 8/2006 | Bovo |
| 2006/0180149 A1 | 8/2006 | Matarasso |
| 2006/0266361 A1 | 11/2006 | Hernandez |
| 2006/0283461 A1 | 12/2006 | Lubke et al. |
| 2007/0016123 A1 | 1/2007 | Jensen |
| 2007/0051364 A1 | 3/2007 | Jacobson et al. |
| 2007/0095349 A1 | 5/2007 | Hansmann et al. |
| 2007/0175478 A1 | 8/2007 | Brunst |
| 2007/0227542 A1 | 10/2007 | Kashmakov et al. |
| 2007/0283962 A1 | 12/2007 | Doshi et al. |
| 2007/0287976 A1 | 12/2007 | Sherrill |
| 2008/0023007 A1 | 1/2008 | Dolezal et al. |
| 2008/0032119 A1 | 2/2008 | Feldhahn et al. |
| 2008/0041397 A1 | 2/2008 | Hirs |
| 2008/0053460 A1 | 3/2008 | Wilson |
| 2008/0087286 A1 | 4/2008 | Jones |
| 2008/0099021 A1 | 5/2008 | Moore |
| 2008/0135044 A1 | 6/2008 | Freitag et al. |
| 2008/0142014 A1 | 6/2008 | Jiang |
| 2008/0142018 A1 | 6/2008 | Doshi et al. |
| 2008/0178874 A1 | 7/2008 | Doshi et al. |
| 2008/0221470 A1 | 9/2008 | Sather et al. |
| 2009/0145441 A1 | 6/2009 | Doshi et al. |
| 2009/0194100 A1 | 8/2009 | Minagi |
| 2009/0194109 A1 | 8/2009 | Doshi et al. |
| 2009/0241965 A1 | 10/2009 | Sather et al. |
| 2009/0308398 A1 | 12/2009 | Ferdinand et al. |
| 2010/0326447 A1 | 12/2010 | Loomas et al. |
| 2011/0005520 A1 | 1/2011 | Doshi et al. |
| 2011/0005528 A1 | 1/2011 | Doshi et al. |
| 2011/0005529 A1 | 1/2011 | Doshi et al. |
| 2011/0005530 A1 | 1/2011 | Doshi et al. |
| 2011/0056499 A1 | 3/2011 | Doshi et al. |
| 2011/0067708 A1 | 3/2011 | Doshi et al. |
| 2011/0067709 A1 | 3/2011 | Doshi et al. |
| 2011/0108041 A1 | 5/2011 | Sather et al. |
| 2011/0203598 A1 | 8/2011 | Favet et al. |
| 2011/0218451 A1 | 9/2011 | Lai et al. |
| 2011/0240032 A1 | 10/2011 | Doshi |
| 2011/0240038 A1 | 10/2011 | Doshi et al. |
| 2012/0055488 A1 | 3/2012 | Pierce et al. |

FOREIGN PATENT DOCUMENTS

| | | |
|---|---|---|
| EP | 1205203 A2 | 5/2002 |
| EP | 1481702 A2 | 12/2004 |
| FR | 2862614 A1 | 5/2005 |
| GB | 2096574 A | 10/1982 |
| GB | 2324729 A | 4/1998 |
| JP | 52-123786 A | 10/1977 |
| JP | 55-122742 U | 9/1980 |
| JP | 58-136345 A | 8/1983 |
| JP | 63-189257 U | 12/1988 |
| JP | 7-47126 | 2/1995 |
| JP | 3059270 U | 3/1999 |
| JP | 2001-299916 A | 10/2001 |
| JP | 2002-153489 A | 5/2002 |
| JP | 2002-219174 A | 8/2002 |
| JP | 2002-345963 A | 12/2002 |
| JP | 2002-345966 | 12/2002 |
| JP | 05/40589 A | 2/2005 |
| JP | 2005-505355 | 2/2005 |
| JP | 2008-136496 | 6/2008 |
| JP | 2008-522763 | 7/2008 |
| RU | 2048820 C1 | 11/1995 |
| SU | 1586709 A1 | 8/1990 |

(56) References Cited

FOREIGN PATENT DOCUMENTS

| | | |
|---|---|---|
| WO | WO 90/12614 A1 | 11/1990 |
| WO | WO 93/08777 A1 | 5/1993 |
| WO | WO 95/17220 A1 | 6/1995 |
| WO | WO 95/33520 A1 | 12/1995 |
| WO | WO 98/46310 A2 | 10/1998 |
| WO | WO 99/03395 A1 | 1/1999 |
| WO | WO 00/29066 A1 | 5/2000 |
| WO | WO 00/50121 A1 | 8/2000 |
| WO | WO 00/67848 A1 | 11/2000 |
| WO | WO 01/02042 A1 | 1/2001 |
| WO | WO 01/13839 A1 | 3/2001 |
| WO | WO 01/13908 A2 | 3/2001 |
| WO | WO 01/49371 A2 | 7/2001 |
| WO | WO 01/87170 A1 | 11/2001 |
| WO | WO 01/89381 A1 | 11/2001 |
| WO | WO 02/38038 A2 | 5/2002 |
| WO | WO 03/022124 A2 | 3/2003 |
| WO | WO 03/034927 A1 | 5/2003 |
| WO | WO 2004/084998 A1 | 10/2004 |
| WO | WO2005/000805 A2 | 1/2005 |
| WO | WO2006/040585 A1 | 4/2006 |
| WO | WO2007/023607 | 3/2007 |
| WO | WO 2007/129814 A1 | 11/2007 |
| WO | WO 2007/134458 A1 | 11/2007 |
| WO | WO 2007/146133 A2 | 12/2007 |

OTHER PUBLICATIONS http://chinookmed.com/index.cfm/fa/product.display&Product_ID=275; accessed Nov. 28, 2007.

Mahadevia, A. K. et al., Effects of expiratory positive airway pressure on sleep-induced respiratory abnormalities in patients with hypersomnia-sleep apnea syndrome, Am Rev Respir Dis 1983, vol. 128, pp. 708-711, Oct. 1983.

Dillard, D. et al., Evaluation of a novel intra-bronchial valve to produce lung volume reduction, World Congress of Bronchology, Jun. 2002 (figs. 1-4 available upon request).

Hakel et al.; Nasal obturator for velopharyngeal dysfunction in dysarthria: technical report on a one-way valve; Journal of Medical Speech-Language Pathology; vol. 12; No. 4; pp. 155-159; 2004.

Suwaki et al.; Nasal speaking valve: a device for managing velopharyngeal incompetence; Journal of Oral Rehabilitation; vol. 35; pp. 73-78; 2008.

Suwaki et al.; The effect of nasal speaking valve on the speech under experimental velopharyngeal incompetence condition; Journal of Oral Rehabilitation; vol. 35; pp. 361-369; 2008.

Doshi et al., U.S. Appl. No. 13/545,865 entitled "Nasal Devices," filed Jul. 10, 2012.

Witt et al.; U.S. Appl. No. 61/141,251 entitled "System, Method, and Respiration Appliance for Supporting the Airway of a Subject," filed Dec. 30, 2008.

Flappers are thickened by extra layer. Extra thickness stabilizes them in turbulent airflow

LAYERED NASAL RESPIRATORY DEVICES

CROSS REFERENCE TO RELATED APPLICATIONS

This patent application claims priority to U.S. Provisional Patent Application No. 61/349,139, titled "LAYERED NASAL RESPIRATORY DEVICES", filed on May 27, 2010, and to U.S. Provisional Patent Application No. 61/361, 275, titled "CONFIRMING COMPLIANCE IN OPERATION OF NASAL RESPIRATORY DEVICES," filed on Jul. 2, 2010. Both of these applications are herein incorporated by reference in their entirety.

This application may be related to U.S. patent application Ser. No. 11/759,916, titled "LAYERED NASAL DEVICES," filed on Jul. 7, 2007, U.S. Publication No. 2007/0283962.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

The devices and methods described herein are configured to increase the resistance to exhalation more than the resistance to inhalation. These devices and methods are useful to treat breathing disorders, including sleep disorders such as apnea and snoring. Also described herein are methods and devices for monitoring the compliance with use of nasal devices that are configured to increase the resistance to exhalation more than the resistance to inhalation.

BACKGROUND OF THE INVENTION

A nasal respiratory device as described herein may be used to treat a subject with a respiratory disorder, including, but not limited to, sleeping disorders such as apnea (including OSA), COPD, snoring, and the like.

Obstructive sleep apnea (OSA) is a disruption of a subject's breathing during sleep. If left untreated, sleep apnea can be life-threatening. Further, OSA may lead to sleep deprivation and a resultant decrease in alertness. Thus, OSA may pose a significant public health issue, as it has a higher prevalence among those engaged in the trucking and transportation industries as compared to the general population.

Currently, the most widely recommended treatment for sleep apnea is continuous positive airway pressure (CPAP). CPAP involves the active application of pressurized airflow, and requires that the patient wear a mask-like device while sleeping; the mask directs the positive airflow into the patient's airway in order to prevent the airway from collapsing. Despite the positive aspects of CPAP treatment, patient compliance has proven difficult to achieve. CPAP can cause nasal congestion, claustrophobic sensations, and other side effects. Patients frequently complain of the discomfort of wearing the mask while sleeping, as well as the noise and constriction of the air supply. Adequate compliance is being recognized increasingly as a major determinant of treatment success, and various strategies have been employed to enhance compliance with CPAP. Compliance is further confounded because patients may remove the CPAP mask as they are falling asleep or after sleeping with the mask for a short period of time. Most CPAP devices now contain circuitry that records hours of usage and the pressure at any given time. Software tools may be used to help the respiratory therapist monitor how patients are using CPAP.

Recently, passive nasal respiratory devices have been developed which may be used in place of (or in conjunction with) active nasal respiratory devices such as CPAP. For simplicity, these passive nasal respiratory devices are referred to herein as simply "nasal respiratory device" or "nasal devices". In general, these nasal respiratory devices are configured to inhibit exhalation more than inhalation in a sleeping patient. The resistance to exhalation may be considered "passive," since it is applied by a passive airflow resistor, rather than relying on the active application of force (e.g., air). The nasal respiratory devices may be configured to provide resistance to either or both exhalation and inhalation within a specified therapeutic range or ranges for the treatment of apnea, snoring, or other disorders. As used herein, a patient may be any subject, human or non-human, in need of the nasal respiratory ("nasal") devices described herein or in the incorporated references. These devices may be provided as prescription or non-prescription ("over the counter") devices.

Such nasal respiratory devices have been well-described in the following patents and patent applications, each of which is herein incorporated by reference in its entirety: U.S. patent application Ser. No. 11/805,496, titled "NASAL RESPIRATORY DEVICES," filed on May 22, 2007, now U.S. Pat. No. 7,856,979; U.S. patent application Ser. No. 11/759,916, titled "LAYERED NASAL DEVICES," filed on Jun. 7, 2007, now U.S. Publication No. 2007/0283962; U.S. patent application Ser. No. 11/298,339, titled "RESPIRATORY DEVICES," filed on Dec. 8, 2005, now U.S. Pat. No. 7,798,148; U.S. patent application Ser. No. 11/298,362, titled "METHODS OF TREATING RESPIRATORY DISORDERS," filed on Dec. 8, 2005, now U.S. Pat. No. 7,735,491; U.S. patent application Ser. No. 11/298,640, titled "NASAL RESPIRATORY DEVICES," filed on Dec. 8, 2005, now U.S. Pat. No. 7,735, 492; U.S. patent application Ser. No. 12/141,875, titled "ADHESIVE NASAL RESPIRATORY DEVICES," filed on Jun. 18, 2008, now U.S. Publication No. 2007/0050144; U.S. patent application Ser. No. 11/811,401, titled "NASAL RESPIRATORY DEVICES FOR POSITIVE END-EXPIRATORY PRESSURE," filed on Jun. 7, 2007, now U.S. Pat. No. 7,806,120; U.S. patent application Ser. No. 11/941,915, titled "ADJUSTABLE NASAL DEVICES," filed on Nov. 16, 2007, now U.S. Publication No. 2008/0178874; U.S. patent application Ser. No. 11/941,913, titled "NASAL DEVICE APPLICATORS," filed on Nov. 16, 2007, now U.S. Publication No. 2008/0142018; U.S. patent application Ser. No. 11/811,339, titled "NASAL DEVICES," filed on Jun. 7, 2007, now U.S. Pat. No. 7,506,649; U.S. patent application Ser. No. 12/044, 868, titled "RESPIRATORY SENSOR ADAPTERS FOR NASAL DEVICES," filed on Mar. 7, 2008, now U.S. Pat. No. 7,506,649; U.S. patent application Ser. No. 12/369,681, titled "NASAL DEVICES," filed an Feb. 11, 2009, now U.S. Publication No. 2009/0188493; U.S. patent application Ser. No. 12/364,264 titled "CPAP INTERFACE AND BACKUP DEVICES," filed on Feb. 2, 2009, now U.S. Publication No. 2009/0194109; U.S. patent application Ser. No. 12/329,271, titled "PACKAGING AND DISPENSING NASAL DEVICES," filed on Dec. 5, 2008, now U.S. Publication No. 2009/0145788; U.S. patent application Ser. No. 12/329,895 titled "DELAYED RESISTANCE NASAL DEVICES AND METHODS OF USE," filed on Dec. 8, 2008, now U.S. Publication No. 2009/0145441; U.S. patent application Ser. No. 12/405,837, titled "NASAL DEVICES WITH NOISE-REDUCTION AND METHODS OF USE," filed on Mar. 17, 2009, now U.S. Publication No. 2009/0241965; U.S. patent application Ser. No. 12/485,750, titled "ADJUSTABLE RESISTANCE NASAL DEVICES," filed on Jun. 16, 2009, now U.S. Publication No. 2009/0308398; and PCT Patent Application Serial No. PCT/US2009/056948, titled "NASAL DEVICES, SYSTEMS AND METHODS," filed on Sep. 15, 2009, now International Publication No. WO 2010/031040.

In general, these nasal respiratory devices are configured to inhibit exhalation more than inhalation in a sleeping patient. The resistance to exhalation may be considered "passive," since it is applied by a passive airflow resistor, rather than relying on the active application of force e.g., air). The nasal respiratory devices may be configured to provide resistance to either or both exhalation and inhalation within a specified therapeutic range or ranges for the treatment of apnea, snoring, or other disorders. As used herein, a patient may be any subject, human or non-human, in need of the nasal respiratory ("nasal") devices described herein or in the incorporated references. These devices may be provided as prescription or non-prescription ("over the counter") devices.

These patents and patent applications generally describe nasal respiratory devices and methods for treating a variety of medical conditions through the use of such devices, and are not limited to apnea (e.g., obstructive, central, complex and mixed apnea). These medical conditions include but are not limited to snoring, Cheyne Stokes breathing, UARS, COPD, hypertension, asthma, GERD, heart failure, and other respiratory and sleep conditions. Such nasal respiratory devices typically induce positive end-expiratory pressure ("PEEP") and/or expiratory positive airway pressure "EPAP"), and are adapted to be removably secured in communication with a nasal cavity. Similarly, the respiratory devices described herein may include devices having one or more expiratory resistor valves.

These devices may include an opening (which may form a passageway), an airflow resistor (e.g., valve) in communication with the opening, and a holdfast to secure the device in communication with a nostril, nasal opening and/or nasal passage. For example, the holdfast may be configured to removably secure the respiratory device within (or over or around) the nasal cavity. The airflow resistor (which may be a valve) is typically configured to provide greater resistance during exhalation than during inhalation.

Although general descriptions of these devices have been described both functionally and by example, certain variations of nasal respiratory devices have not previously been described. Thus, it may be beneficial to improve upon the devices, kits and methods previously described, and particularly to more fully develop certain embodiments of nasal devices and methods of arranging, using, manufacturing, inserting and removing nasal respiratory devices. Described below are specific variations of nasal devices, methods of using nasal devices and kits including such nasal devices.

For example, it would be beneficial to provide nasal devices that are adapted for ease of use, including application. It would also be beneficial to provide nasal devices that more readily form a seal. It would also be beneficial to provide nasal devices that are quiet, or minimize the noise of operation when the subject is breathing through the device, particularly in a low-profile layered) nasal device, such as those described herein. Finally, it would be beneficial to provide nasal devices that may be economically fabricated or manufactured, including nasal devices that are fabricated from a limited number of parts or layers. It would also beneficial to provide nasal devices that may be fabricated inexpensively with high tolerance and reproducibility.

The nasal devices, kits, systems and methods described herein address many of the potential benefits described above. In particular, the nasal devices described herein are passive nasal devices having a low profile that may be fabricated economically, and may have reduced operation noise, while still inhibiting exhalation more than inhalation with a therapeutically relevant range of resistances.

Further, the nasal devices described herein are typically more comfortable, less expensive, and easier to use than the CPAP and other active respiratory devices (e.g., devices or systems that actively apply air or airflow). It may also be desirable to monitoring compliance for patient treatment with these devices. Thus, it may be beneficial to provide devices, systems and methods for monitoring usage/compliance of any of these passive respiratory devices. Described herein are devices, systems and methods that may address this need and allow monitoring of compliance and/or use of the passive nasal devices described.

SUMMARY OF THE INVENTION

The present invention relates to nasal devices including layered nasal devices, as well methods of forming and manufacturing nasal devices. The nasal devices and methods of making and using them described herein may include any or all of the following improvements: the nasal device may include an integrated flap-valve and holdfast base layer; the nasal device may include a noise-reduction element; the nasal device may include a valve cone (e.g., "rim body") on at least one side of the nasal device. In some variations the valve cone is an alignment feature one side (e.g., the subject-facing side) of the device that is configured to help the subject align the device with the nostril opening(s) when applying the device.

For example, described herein are layered nasal devices that may be formed of four or fewer layers. The devices may include essentially four layers: a first layer forming both a holdfast base and a flap, a valve limiting layer, a rim body extending from the first layer, and an adhesive layer between the limiting layer and the airflow resistor layer. The flap and the valve limiting layer typically form an airflow resistor that is configured to have a greater resistance to exhalation than inhalation when the device is worn. The holdfast base may include an adhesive. In some variations, the adhesive is a layer that is applied to the holdfast base during fabrication. The adhesive layer may include a core layer of material (e.g., polymer, fabric, etc.) in between two sticky surfaces.

In general, these nasal devices may be adhesively secured over one or (in some variations) both of a subject's nostrils.

For example, described herein are nasal devices for inhibiting exhalation more than inhalation. The nasal device may include: a first layer comprising a flap portion and a holdfast portion; a flap limiting layer adjacent to the flap portion, wherein the flap limiting layer and the flap portion form an airflow resistor configured to inhibit exhalation more than inhalation; and a rim body extending from at least one side of the layer and at least partially surrounding the airflow resistor.

The flap portion may include a plurality of flaps. The flap(s) may be cut (e.g., die cut, laser cut, etc.) from the layer. The flaps may be cut so that there is a predetermined spacing between the flap and the rest of the layer, providing a leak pathway, allowing a base level of airflow through the device even when the airflow resistor is closed (e.g., during exhalation). In some variations the device includes an opening that acts as a predetermined leak pathway. This opening may be cut through the first layer.

The first layer is typically a flexible material, and may be formed of any appropriate material, including polymers, fabrics, or the like. For example, the first layer may be formed of a thin layer of urethane. In some variations the first layer is adhesive, or includes an adhesive on at least one side. In some variations, the adhesive is added to the first layer (e.g., during processing). For example, and adhesive may be applied to the first layer (and particularly the holdfast portion or a part of the holdfast portion). Thus, the holdfast portion of the first layer may include an adhesive material.

In some variations, an adhesive that is applied to the holdfast portion of the first layer includes a support or core region or layer formed of a flexible or semi-rigid material. The core may be formed of a polymer or other material, including fabrics. The core layer may be colored or textured, and may be of a thickness sufficient to add stiffness or support to the holdfast region. The core is typically a layered (e.g., relatively thin and flat) material that may include adhesive on both sides (e.g., such as a double-sided tape). Any appropriate adhesive, but particularly biocompatible adhesives, may be used. Thus, the adhesive comprises a core region having an adhesive on either side.

In some variations, the adhesive including a core region or layer may be applied to the holdfast region of the device to provide additional support or stiffness, and improve handling since the holdfast region formed of the layer (e.g., the first layer) maybe very thin.

The holdfast region may generally be flexible and conforming to the subject. For example, the holdfast region (including any adhesive/core added) may form a seal securing the nasal device in communication with the subject's nasal cavity and/or opening, so that respiration through one or both nostrils must pass through the nasal device when the device is being worn.

The flap limiter (flap limiting layer) may be a mesh, or a more structural (e.g., stiffer) support, such as a frame. In general the flap limiting layer is positioned adjacent to the flap(s) so that it may prevent them from opening in one direction, e.g., during exhalation. The flap limiting layer may be secured in position using an adhesive, such as a ring of adhesive. The ring of adhesive may surround the flap(s).

The devices described herein may also be configured so that they allow increase airflow during exhalation at relatively high pressures, for example, when the pressure seen by the airflow resistor during exhalation exceeds a threshold pressure level. For example, in some variations the flap valve limiter (or valve limiting layer) may be configured to allow the flap valve to open at least slightly when the pressure exceeds a threshold level. Thus, at high pressures the otherwise closed flap valve(s) is permitted to open a little. In some variations this is achieved by configuring the flap limiting layer to deform or be displaced at high (greater than a non-zero threshold) pressure levels. In one variation, the valve limiting layer is a mesh having a large pore size; as the pressure exceeds a threshold value, the flaps deform into the pore, increasing the expiratory flow through the nasal device. In some variations, the flap limiting layer is held adjacent to the flaps some fixed distance by a spring force that can be overcome above a threshold pressure; overcoming the spring force allows the flap limiting layer to move further from the flaps, allowing them to open at least slightly during exhalation. Thus in some variations of the nasal devices described herein the nasal devices are configured as PEEP (positive end expiratory pressures) valves.

As mentioned, the flap portion may include multiple flaps cut from the layer. The multiple flaps may be separate from each other (e.g., multiple "fish scale" type flaps, or they may be connected to each other (e.g., pie-slide type flaps). In some variations, the nasal device includes one or more openings forming a leak pathway through the nasal device. The flaps may be cut or formed so that there spaces between the flap edge and the rest of the device (e.g., the layer and/or flap limiting layer) forming a leak pathway.

Any of the nasal devices described herein may include a rim body. The rim body may extend from the layer (e.g., the holdfast region) and may protect and at least partially surround the airflow resistor. In some variations the rim body is a single (e.g., upper rim body) extending out of the first layer forming the flap and the holdfast region. This upper rim body may be used to help position the nasal device within the nose. The rim body may be shaped conical, curved, etc.) for comfort and/or to provide noise reduction. The upper rim body therefore may be positioned on the side of the nasal device that is in contact with the subject, so that the rim body is positioned within a nostril opening. The upper rim body may be formed of any appropriate material, including a polymeric material. For example, the upper rim body may be thermoformed during manufacture as it is adhesively secured to the nasal device. In some variations, a lower rim body extends from the opposite side of the first layer, away from the rim body.

The upper rim body (e.g., a structure extending up from the plane of the airflow resistor on the side of the device facing towards the subject when the device is worn by the subject) may be configured as an alignment member. As mentioned, this alignment member may aid in aligning the device with the subject's nostril opening when applying the device to be worn.

Any of the nasal devices described herein may include one or more noise reduction features or elements. For example, the flaps may be formed as noise-reduction flaps. Noise-reduction flaps may be thick (or may including a thickened region) to prevent or tower vibration. In some variations, the shape of flaps is a noise-reduction feature. Flaps having an approximately rectangular shape, with gradually curved or rounded edges may be preferred to (and more noise-reducing then) flaps having more angular edges. In some variations, the nasal device may include a rim body (e.g., the upper rim body) that is configured to contact the tip of the flap or flaps when the device is open (e.g., during inhalation) to prevent vibration of the tip that may lead to buzzing.

Also described herein are nasal devices for inhibiting exhalation more than inhalation. A nasal device may include: a layer comprising a flap portion and a holdfast portion (e.g., a first layer); a flap limiting layer adjacent to the flap portion, wherein the flap limiting layer and the flap portion form an airflow resistor configured to inhibit exhalation more than inhalation; a rim body extending from one side of the layer and at least partially surrounding the airflow resistor; and a noise reduction feature configured to minimize noise as air is drawn through the device.

As mentioned above, a noise-reduction feature may include projections on the rim body. Any of the herein mentioned noise-reduction features (e.g., projections, shaped flaps, flap thickeners, etc.) may be included.

Also described herein are methods of forming a nasal device, or of manufacturing a nasal device. The methods described herein may be particularly useful for forming low-cost nasal devices that have the appropriate airflow resistance (e.g., high expiratory and low inspiratory resistances) for therapeutic use. Thus, in the manufacturing methods describe herein may allow for the assembly of a nasal device with the minimum number of parts and/or steps, while still forming a robust nasal device.

For example, described herein are method of forming a nasal device including the steps of: cutting a first layer of flexible material to form one or more flaps and a holdfast base; securing a flap limiter adjacent to the one or more flaps so that the flap limiter and the flaps form an airflow resistor configured to inhibit exhalation more than inhalation; and securing a rim body around the one or more flaps so that the rim body extends from the first layer. The order that these steps are performed may be as listed, or may be different. For example, the step of cutting the first layer to form the flaps may be performed before or (in some variations) after securing the flap limiting layer, or before or after securing the rim body. Preferably, however, the flaps are cut before securing the limiting layer and rim body.

In general, the nasal devices described herein may be formed as part of an automated (e.g., "assembly line") process to allow efficient mass-production. For example, rolls or sheets of raw material (e.g., material for the first layer, the flap limiter layer, the adhesive, the rim body, etc.) may be aligned in register for sequential processing and assembly.

Additional steps may be performed. For example, in some variations the method may also include the step of applying an adhesive to the holdfast base. Alternatively, in some variations the first layer (or a portion of the first layer) may already be adhesive, or may include an adhesive.

The step of securing the rim body may include adhesively securing the rim body to the first layer. For example, the rim body maybe attached to the adhesive portion of the first layer by simply pressing down on the rim body.

In some variations, the rim body is thermoformed as part of the method of fabricating the device. Thermoforming may be done in-line, during the assembly process. Thus the rim body may be shaped and adhere to the rest of the device as part of an automated assembly process.

As mentioned briefly above, passive nasal devices, including those described herein, may be configured or adapted for use with one or more devices or systems for monitoring compliance/use of the devices by subjects. For example, also described herein are devices, systems and methods to confirm use of a nasal respiratory device, and particularly passive nasal respiratory devices having an airflow resistor configured to inhibit exhalation more than inhalation and a holdfast configured to secure the nasal device in communication with a subject's nose (e.g., at least partially over, around and/or in the subject's nose). The methods, systems and devices for monitoring or confirming use of the nasal device may be referred to as methods, systems and devices for determining and/or monitoring compliance. For example, any of the devices described herein may be used to confirm that a subject (e.g., a patient) has been wearing and/or using a nasal device while sleeping or during the day. This compliance or use information may be stored and/or analyzed either locally while in possession of the subject, or it may be stored and/or analyzed remotely. Remote information may be provided by the subject or an agent of the subject (e.g., self-reporting) who may provide data or may send used devices or packaging to a remote monitoring location, or it may be provided automatically by a system device which is configured to process and/or pass on the monitoring information.

For example, described herein are methods of confirming usage of a nasal respiratory device that may include the steps of receiving an indicator of use of the nasal respirator device, wherein the device comprises an airflow resistor configured to inhibit exhalation more than inhalation, and a holdfast configured to secure the nasal device in communication with a subject's nose; and determining if the subject has worn the nasal device. In general, the method of confirming usage of a nasal respiratory device may be specifically for confirming home usage of a nasal respiratory device, e.g., away from a hospital or clinical setting.

The step of receiving may include receiving monitoring information from one or more sensors. For example, the information received may be monitoring information that would be indicative of the subject wearing the device and/or breathing through the device. The monitoring information may include one or more or: strain data, temperature data, chemical data, moisture data, or the like. Any appropriate sensor may be used, particularly sensors indicating either contact with the patient or respiration by the patient (i.e., through the device). The sensor may be selected from the group consisting of strain gauge, chemical sensor, temperature sensor, pH sensor, galvanic sensor, etc.

In some variations, the step of receiving comprises receiving patient-reported information. The patient-reported information may include comprise visual information (e.g., a photograph of the device or a portion of the device), or information extracted from the nasal device. For example, the nasal device may include an identified (e.g., alphanumeric identifier, color, etc.) that is exposed upon using the device, either immediately upon removing the device from the packaging or after wearing the device for some period of time.

In some variations, the step of receiving comprises receiving the nasal respiratory device and examining the nasal respiratory device. For example, the nasal respiratory device (or the packaging of the device, may be analyzed after the subject has worn the device. The analysis may be performed either remotely, by sending the device and/or packaging or a portion of the device to a remote analysis location, or it may be performed locally. For example, when the device is analyzed locally, the subject may use a device that examines the nasal device to determine if (and possibly for how long) it has been worn. The local monitoring device may store and/or transmit this data, and may keep a compliance log. Such a monitoring device may include one or more alarms, including alarms to indicate non-compliance or compliance.

In embodiments using a remote analysis of compliance, the subject may send the device or a portion of the device (e.g., by mail or shipping) to a remote monitoring center that has the capability (e.g., a remote monitoring device to determine compliance or otherwise confirm use.

For example, a remote monitoring device may include an analyzer that is configured to analyze the nasal respiratory device. The remote monitoring device may be configured to log use of the nasal respiratory device. Either the remote or local monitoring device may be configured to determine if the subject has been using the nasal device based on the received information. For example, a monitoring device may include an ultraviolet light that causes the device to fluoresce if it has been in contact with skin (e.g., oils on the subject's skin). Devices that have not been worn will not fluoresce. In some variations, the nasal devices may include an indicator that reacts when exposed to skin and/or respiration so as to provide feedback that the device has been worn (or for how long the device was worn). For example, in variations including an adhesive holdfast, the adhesive may include a pH-sensitive material that reacts to a quantifiable degree with worn in contact with skin.

Any of the systems and methods described herein may be configured for determining the efficacy of the nasal device. For example, the devices or systems described herein may indicate or confirm flow through the device, or that exhalation (i.e., expiratory flow) was limited or restricted relative to inhalation flow.

Also described here are systems for confirming usage of a nasal respiratory device, the system comprising: a nasal respiratory device comprising an airflow resistor configured to inhibit exhalation more than inhalation, and a holdfast configured to secure the nasal device in communication with a subject's nose; and a sensor configured to provide monitoring information on the use of the nasal device.

The sensor may comprise a strain gauge, a chemical sensor, temperature sensor, pH sensor, or the like. The system may also include an analyzer configured analyze information from the sensor to confirm usage of the nasal respiratory device. In some variations, the system includes a recorder configured to record monitoring information.

Also described herein are devices for confirming usage of a nasal respiratory device, the device comprising: a nasal respiratory device comprising an airflow resistor configured to inhibit exhalation more than inhalation, and a holdfast configured to secure the nasal device in communication with a subject's nose; and an indicator configured to provide an indicator that the device has been applied in communication with the subject's nose.

The indicator comprises an optical indicator (e.g., a colorometric indicator), an alphanumeric indicator, a tamper-evident indicator, a stretch indicator, a heat-sensitive indicator (e.g., body-heat sensitive), or the like.

Also described herein are systems for confirming usage of a nasal respiratory device that include: a nasal respiratory device comprising an airflow resistor configured to inhibit exhalation more than inhalation, and a holdfast configured to secure the nasal device in communication with a subject's nose; and an analyzer configured to examine a nasal respiratory device to determine if the subject has worn the device.

The analyzer may be an optical analyzer (e.g., an ultraviolet light source, etc.), a chemical sensor, etc. In some variations, the analyzer includes a collection box for collection of individual nasal devices as they are worn.

BRIEF DESCRIPTION OF THE DRAWINGS

FIG. 1A is an exploded view of the nasal device, showing a single layer forming the flap valve portion of the airflow resistor and the base of the adhesive holdfast. FIGS. 1B and 1C are cross-sections through a central region of the device shown in FIG. 1A. FIG. 1D is a bottom view (facing away from the patient-contacting surface) of the nasal device shown in FIG. 1A.

FIG. 1E shows an exploded view of the nasal device. A single layer forms the flap valve portion and base of the adhesive holdfast. FIGS. 1F and 1G show views of the top (e.g., subject-facing side) of the device of FIG. 1E and the bottom (e.g., side facing away from the subject) of the device of FIG. 1E, respectively.

FIG. 2A is an exploded perspective view and FIG. 2B is a partial cross-section through the device shown in FIG. 2A.

FIG. 3A is a top perspective view (showing the patient-contacting face of the device), FIG. 3B is an exploded view of the nasal device shown in FIG. 3A. FIG. 3C is a top perspective view of another variation of a nasal device.

FIG. 5A shows a top view of a layer forming a holdfast base and a flap of an airflow resistor and FIG. 5B shows a side perspective view of the layer shown in FIG. 5A, FIG. 5N shows a top view of a layer forming a holdfast base and a flap of an airflow resistor and FIG. 5o shows a side perspective view of the layer shown in FIG. 5N.

FIG. 17A shows a perspective view of a first variations, and FIG. 17B shows an exploded view of the device shown in FIG. 17A. FIG. 17C shows a perspective view of another variation of a nasal device.

FIG. 18A is an exploded view of a first variation of a whole-nose nasal device and FIG. 18B is a top view of another variations of a whole-nose nasal device.

In all of the examples provided herein, the dimensions (shown in inches unless otherwise specified) are only for illustration purposes, and may be different from those shown. For example, any of the dimensions shown may be increased or decreased +/−5%, 10%, 25%, 50%, 100%, 125%, 150%, 200%, etc. the sizes shown.

DETAILED DESCRIPTION OF THE INVENTION

In general, the devices, systems and methods described herein are for nasal respiratory devices that include a holdfast that seals the device in communication with the subject's nasal cavity (e.g., over, within or around the subject's nostril(s)), and an airflow resistor configured to inhibit exhalation more than inhalation.

These devices and methods may provide improvement over previously described nasal devices, however, in particular, the nasal devices described herein may include a combined or integrated holdfast region (or portion of the holdfast) and flap portion of the airflow resistor. Combining elements of the holdfast with elements of the airflow resistor may enhance the operation and the manufacturability of the nasal devices.

In addition, the nasal devices described herein may include a rim body portion (which may also be referred to as a valve cone, and in some variations may be configured as an aligner or alignment element) that extends from the holdfast region of the device and be inserted into the subject's nose. The rim bodies described herein may be thermoformed, and may be adhesively secured to just one side of the nasal device. Securing the rim body (e.g., adhesively) to just one side of the nasal device may also enhance manufacturability while providing a robust device.

Finally, the devices and methods described herein may be designed to reduce operational noise, such as buzzing, humming, clicking or other noises that may be made by the device as the subject breathes through the nasal device. Noise may result because of vibration (e.g., 'flapping') of the edge of the flap valve when air flows through the nasal device. Thus, many of the variations described herein include features that act as noise-reduction elements or features to reduce this noise. In some variations the nasal device includes a region that engages with the edge(s) of the flap during operation (e.g., luring inhalation, when the flap is "opened") to prevent vibration of the edge of the flap.

Figure 1A:
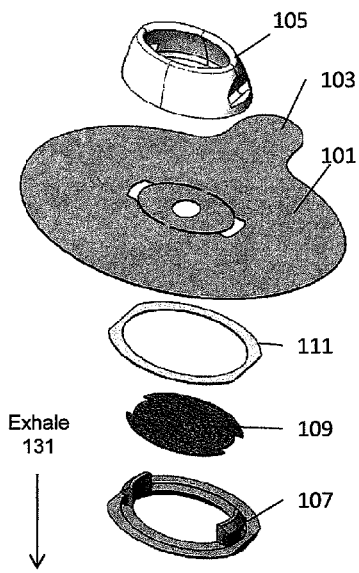
FIGS. 1A-1D illustrate one variation of a nasal device.
Figure 1B:
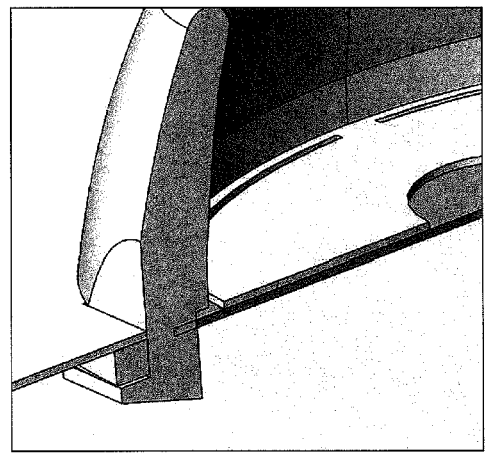
Figure 1C:
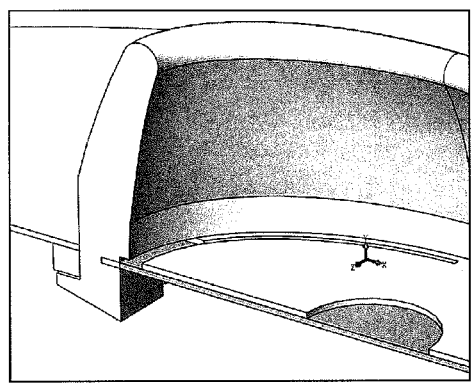
Figure 1D:
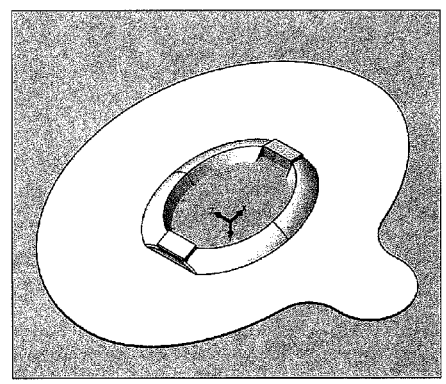

FIGS. 1A-1D illustrate one variation of a nasal device having a shared layer forming the flaps of the airflow resistor and a portion (or the complete) holdfast. FIG. 1A is an exploded view showing the different components making up this variation. In FIG. 1A, the first layer 101 is formed of a urethane layer that is cut to form both the outline of the holdfast region and the flaps of the airflow resistor. In this example, the holdfast includes a grasping region 103 that may help in removing and/or applying the holdfast to the user's skin. The upper surface of the flap vale includes an outer holdfast region that may also include an adhesive (not visible in FIG. 1A). The inner region (surrounded by the holdfast) has been cut to form the flaps, as well as a central opening forming a leak pathway that remains open even when the valve is otherwise closed (e.g., during exhalation). An upper rim body 105 includes snaps or securing regions that pass through cut-outs on the layer to engage a lower rim body 107. In this variation, the upper and lower rim body may be secured together so that they also help secure a valve limiting layer 109 to the rest of the nasal device. The valve limiting layer 109 shown is a mesh layer that is also adhesively secured to the rest of the nasal device by adhesive ring 111. FIGS. 1B and 1C show enlarged sections through this nasal device. FIG. 1D shows a bottom view of the nasal device shown in FIG. 1A, assembled.

Thus, in this example, the nasal device includes five elements: a primary layer forming the holdfast region and the flaps, a valve-limiting mesh layer, an upper rim body and a lower rim body, and an adhesive ring. In some variations, the upper surface of the holdfast region of the layer is an adhesive material, or includes an adhesive. In some variations, an additional element (e.g., a ring of adhesive) may be included. When an additional adhesive is added to the holdfast region of the primary layer, the adhesive may be formed from a double-sided adhesive layer. It may be beneficial to include a double-sided adhesive layer having a center or core formed of a material that may provide additional support and/or thickness to the holdfast region. The core region or layer may be a formed material, a fabric, or the like.

For example, an adhesive may be a transfer adhesive that is applied and then die cut. The transfer adhesive may include a thickness that makes the holdfast thicker and easier to handle, when added to the holdfast region. In some variations, the adhesive is applied during manufacturing. A transferred adhesive may be formed like a double-sided tape, to have a core region (layer) that is formed of a fabric or other material having adhesive (e.g., a biocompatible adhesive) on both sides. The fabric may be flexible and may be colored and/or textured. A colored fabric may be skin-toned (in a particular flesh tone), it may be clear, or it may be colored in any appropriate color or pattern.

Figure 1E:
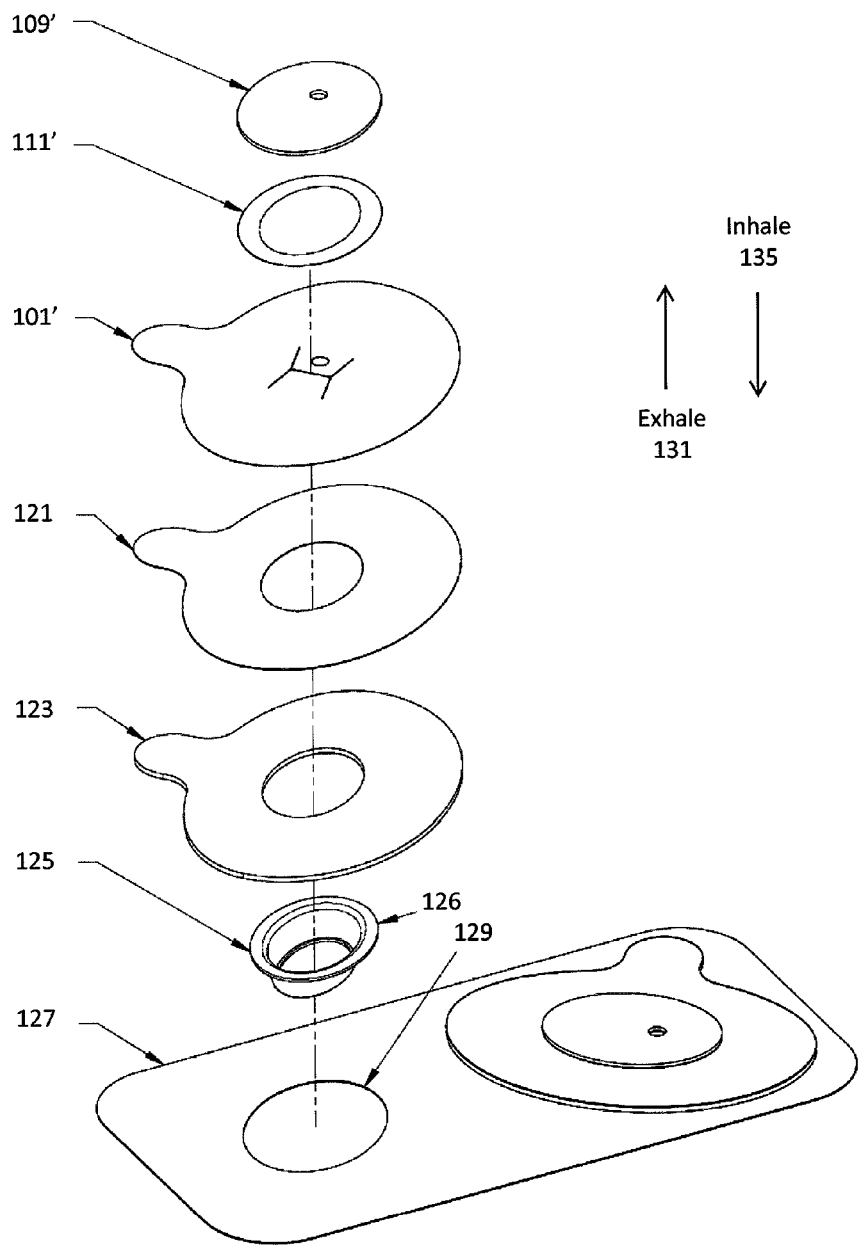
FIGS. 1E-1G illustrate another variation of a nasal device.
Figure 1F:
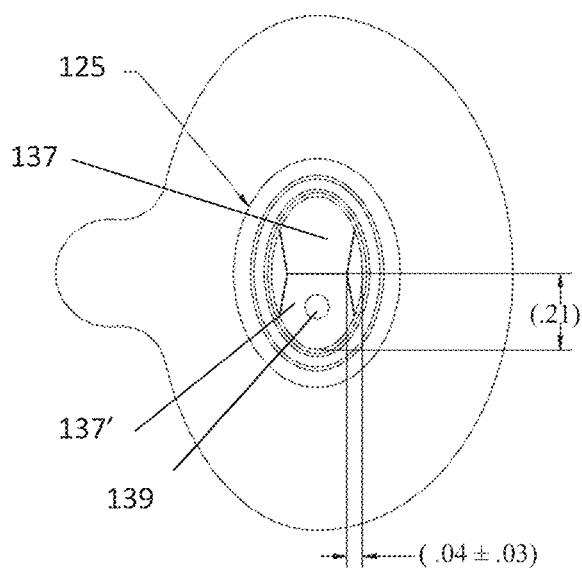
Figure 1G:
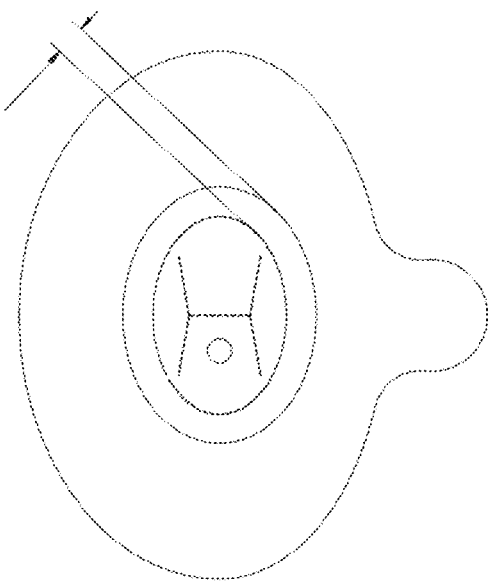

FIGS. 1E-1G illustrate another variation of a nasal device having a shared layer forming the flaps of the airflow resistor and a portion (or the complete) holdfast. FIG. 1E is an exploded view showing different components that may make up this variation. The outermost layer 109' is a valve limiting layer such as a mesh layer that is adhesively secured to the rest of the nasal device by adhesive ring 111', similar to the variation shown in FIG. 1A. The valve layer 109' and adhesive ring 111' may form a sub-assembly (e.g., valve limiting assembly); in some variations, the valve layer does not require the additional adhesive ring 111' to secure to the rest of the device. For example, the device may be heat-staked or fused adjacent to flap valve layer 101'.

The flap valve layer 101' is cut to form both a portion of the holdfast region (e.g., the base of the holdfast region and the flaps of the airflow resistor. This layer may be referred to as a combined flap/holdfast layer 101'. In this example, the flap/holdfast layer is formed out of polyurethane. In FIG. 1E a separate bioadhesive layer 121 is secured to one side of the combined flap/holdfast layer 101' in a region surrounding the flap valve (forming an opening allowing the flap valve in open/close). In some variations, the combined flap/holdfast layer already includes an adhesive surrounding the flap region. For example, an adhesive may be spray coated, pained on, or otherwise formed around the flap valve. In some variations, the adhesive on the combined flap/holdfast may be configured to secure the device directly to a subject's skin; in the example shown in FIG. 1E, and additional adhesive layer 123 (e.g., a core layer) formed of a foam material (e.g., polyethylene foam with acrylic adhesive) is secured to the combined flap/holdfast layer either directly or through the intermediate adhesive layer 121. Any of the device variations may include this foam layer, which may provide some stiffness and/or support to the device when removed from the support backing 127 and may help seal the device against and/or around the subject's nostril. A central opening forming a leak pathway though the flap valve (on the combined flap/holdfast layer 101') and, in some variations the valve limiter layer 109', is also shown. This leak pathway is an opening that may remain open even when the valve is otherwise closed (e.g., during exhalation). An upper rim body 125, configured as an aligner or alignment element is adhesively secured (by flange rim 126) in this example. Any appropriate aligner may be used, including ha the cone-sped element shown here. In some variations, the aligner is a dome shape formed of a mesh having a very large opening; the mesh opening size may be sufficiently large so that it does not substantially interfere with exhalation or inhalation airflow, similar to mesh variations of the valve liming layer 109'. In FIG. 1E, the device(s) are assembled onto (or attached to) a support or backer card 127, which has openings 129 through which the alignment feature 125 extends. In the example shown, two devices (one for each nostril) are shown assembled onto a backer card 127. The devices may be peeled off of the backer card (which typically includes a surface to allow removal, such as a non-stick, smooth or waxy surface) and applied to the nostrils, using the aligner as a guide so that the aligner is inserted at least partially into the nostril opening. The subject may then breathe through the device so that exhalation and inhalation occur through the device in the directions shown by arrows 131 and 115.

FIGS. 1F and 1G show top (subject-facing) and bottom (facing away from the subject) views, respectively. In FIG. 1F, for example, the alignment cone (aligner 125) is within the subject's nostril when worn, and the flap valves 137, 137' are closed during exhalation (though the leak path 139 remains open) and the flap valves 137, 137' open during inhalation.

Thus, in this example, the nasal device assembly includes six elements: a primary layer forming the combined flap/holdfast layer 101', a valve-limiting mesh layer 109', an adhesive ring 111', a holdfast adhesive ring layer 121, a foamed adhesive holdfast layer 123, and an aligner 125. As mentioned, in some variations, all or part of the combined flap/holdfast layer 101' may be adhesive, which may eliminate the need for the separate adhesive rings 111' and/or 121; alternatively the foamed holdfast layer (if included) may be adhesive on both sides. The aligner 125 may be secured to the combined flap/holdfast layer or any of the other intervening layers. In some variations it may be beneficial to form a holdfast subassembly including the combined flap/holdfast layer 101' and any or all of the adhesive layer 121, foamed holdfast layer 123, and optionally the aligner element 125. Such subassemblies may make it easier to assemble and/or fabricate these devices.

Figure 2A:
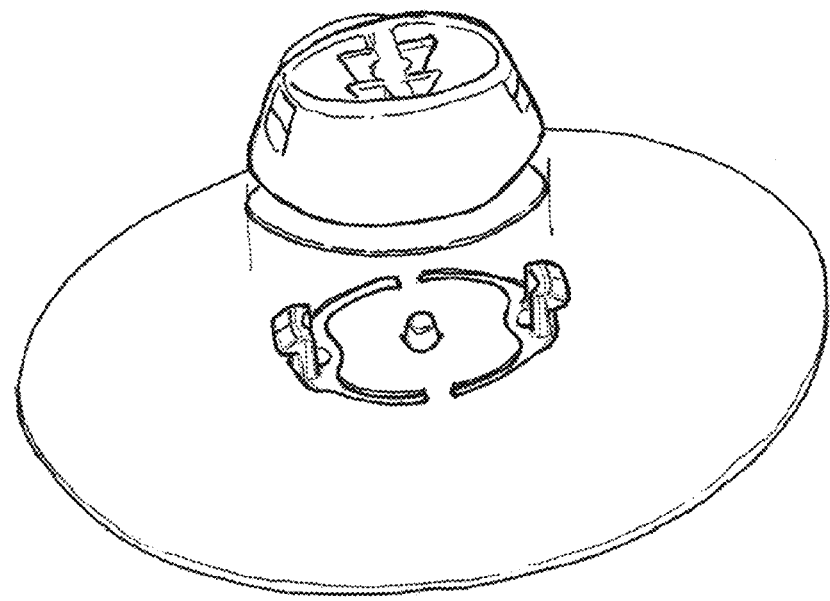
FIGS. 2A and 2B illustrate another variation of a nasal device having an integrated flap and holdfast base.
Figure 2B:
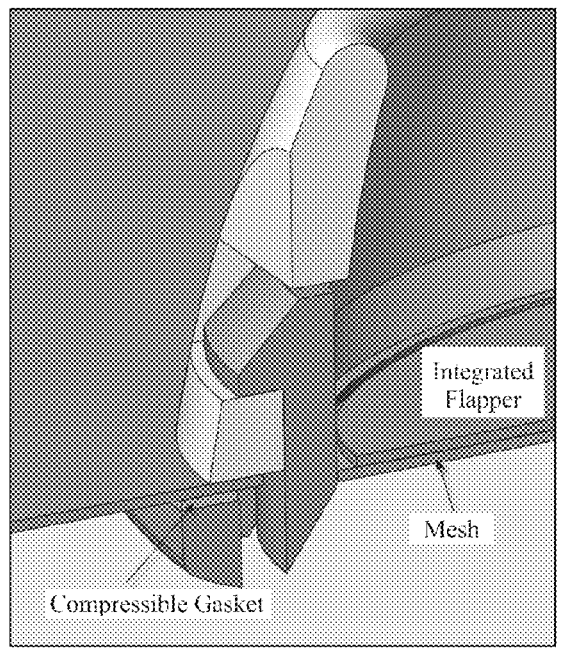

FIGS. 2A and 2B illustrate another variation of a nasal device having a single layer forming the base region of the holdfast and the flap valves, referred to herein as "integrated valves." This embodiment also includes an upper and lower rim body, and includes a gasket between the two that is compressible, and may help secure the rim bodies to the rest of the nasal device and hold the intervening layers (e.g., the valve liming mesh layer) in place.

In some variations, the nasal device includes just an upper rim body (also referred to as a valve cone or valve body), acting as an aligner. This single rim body may be adhesively secured to the integrated layer forming the holdfast and the flaps of the airflow resistor. For example, the adhesive on the upper face of the holdfast may be used to secure the rim body in position. Thus, the rim body my be formed (e.g., thermoformed) to have a flat base region 301 that adheres to the adhesive of the inner perimeter of the holdfast region. The upper rim body (or only rim body) may be thermoformed, as indicated in the figures, to have the slightly inwardly sloping shape extending from the base formed by the holdfast layer.

Figure 3A:
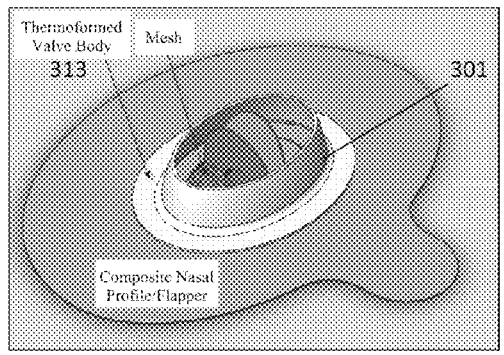
FIGS. 3A-3C illustrate variations of nasal devices having a single rim body element.
Figure 3B:
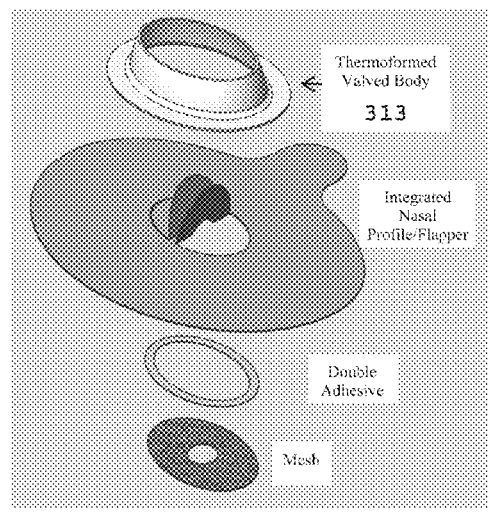

In some variations it may be beneficial to thermoform (or otherwise fabricate or form) the rim in-line during assembly and fabrication of the nasal device. Thermoforming the aligners during fabrication may allow the nasal devices to be assembled in place as they are formed, avoiding the need to "pick and place" the small rim bodies during fabrication which may arise when the rim body is formed separately. As mentioned above, in some variations, the valve body/aligner may include a large opening (as shown in FIGS. 1A and 3A-3B), or they may be formed of a mesh material having a relatively large opening. For example, in some variations the mesh may have large openings that do not inhibiting inhalation/exhalation through the device or otherwise contribute significantly (e.g., greater than 5%, 1%, etc.) to the airflow resistance through the device, but may still be used to align the device. This may prevent the need for cutting openings through the material forming the aligner. Thus, a sheet of material (e.g., mesh material) may be formed into a cone or dome shape such as the cone shape shown in FIGS. 3A-3B (thermoformed valve body 313) and cut just around the periphery to form the flange region that is attached to the nasal device.

The rim body (cone) may be beneficial for alignment and installation of the nasal device. The rim body may also protect the airflow resistor, and particularly the flaps, and may keep the path through the nasal device (through the airflow resistor) relatively clear from any interfering material. This role may be particularly relevant for the single-nostril devices illustrated in FIGS. 3A-3C.

Figure 14:
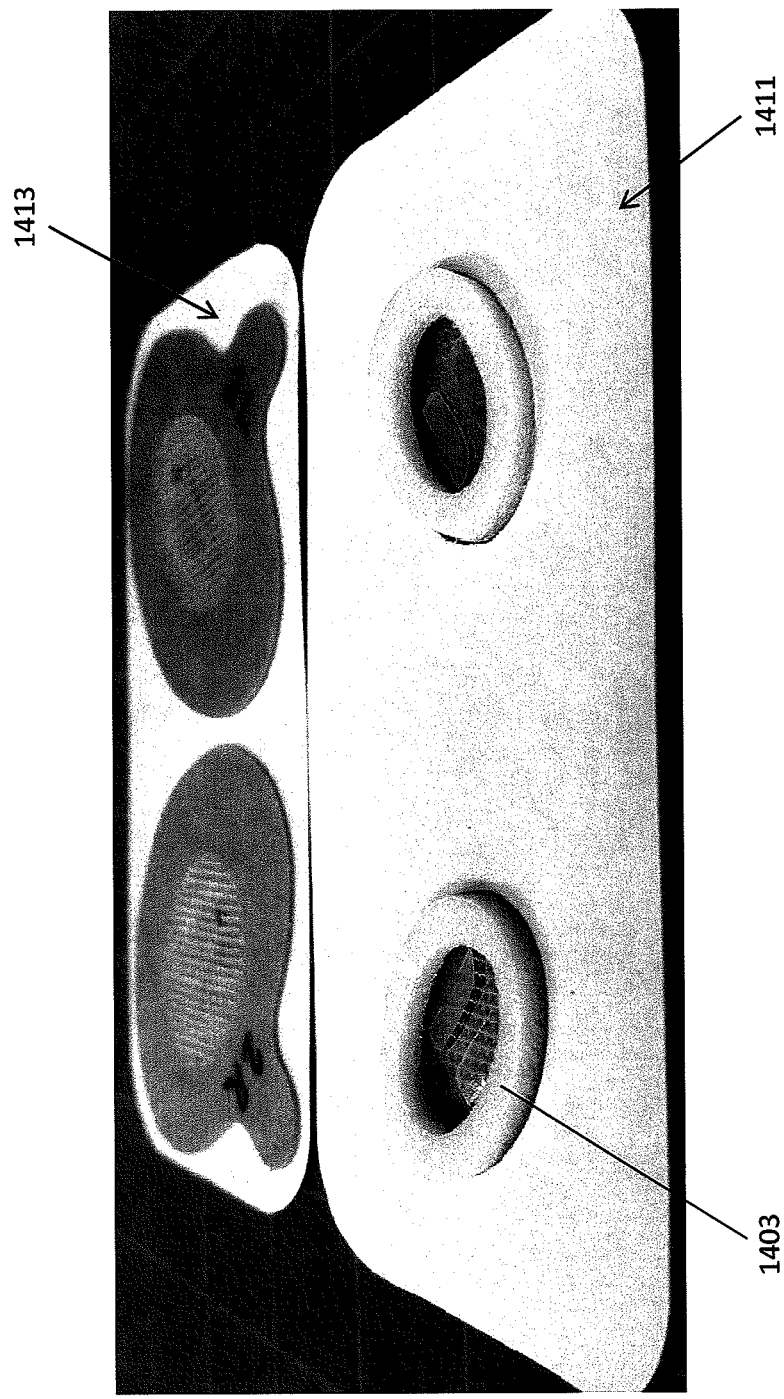
FIG. 14 shows the top and bottom of a pair of devices similar to those described herein, attached to a backer card, in which both devices include an alignment member (aligner) formed of a foamed material extending from the side of the device to be positioned against the subject.

In some variations, such as the variation shown in FIG. 14, the nasal device includes an aligner that is formed of a foamed material. FIG. 14 shows a backer card holding two layered nasal devices. Each nasal device includes an aligner 1403 made of foam that surrounds the airflow resistor region of the device. The aligner 1403 is a ring of foamed material helping to guide placement of the nasal device, white avoiding irritation of the nasal opening. FIG. 14 shows a view of the back of the backer card 1411, with openings for the aligner and through which the airflow resistor may be tested; FIG. 14 also shows a view of the front of the backer card 1413, showing the faces of the two airflow resistors that may be peeled off of the backer card and applied to the subject's face.

Although the same adhesive securing the nasal device to the subject (e.g., the holdfast adhesive) may be used to secure the aligner/rim body to the holdfast, in some variations a separate adhesive may be used to hold this feature in place.

The rim bodies described herein may also help enhance the shelf-life of the nasal devices, normalizing how the device materials behave over time. For example, the stresses on the nasal device, and particularly the airflow resistor portion of the device, may be kept relatively constant by the surrounding rim body region. The rim body may enhance the stability of the device by allowing a more uniform tension across the region within the rim body, including the airflow resistor.

Figure 3C:
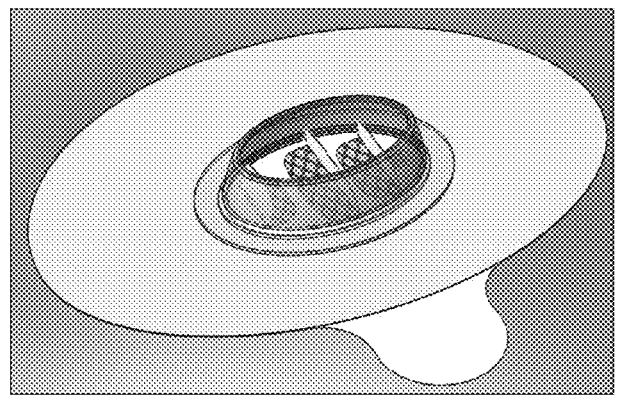
Figure 4:
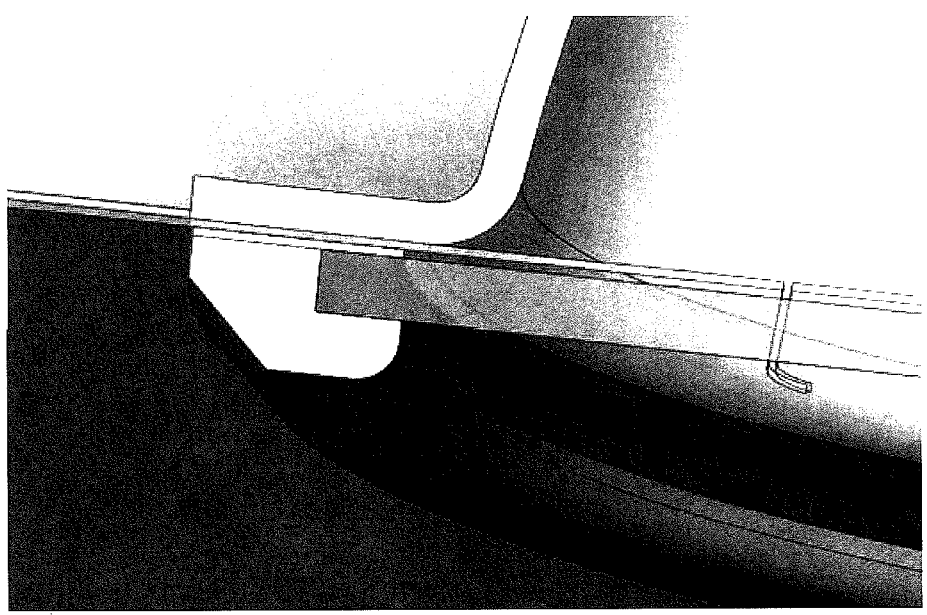
FIG. 4 is a cross-section through another variation of a nasal device.

FIG. 3C illustrates another variation of a nasal device having a single rim body or cone, surrounding an airflow resistor comprising three flaps ("fish scale" style flaps), shown open in FIG. 3C (e.g., mimicking inhalation). The mesh layer behind the flaps as a flap limiter or liming layer to prevent opening during exhalation.

Figure 5A:
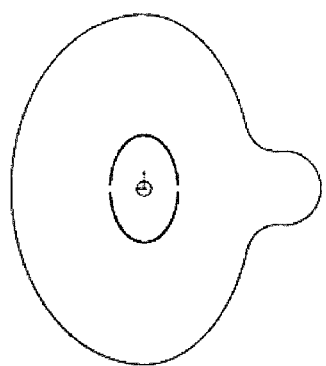
FIGS. 5A-5o illustrate variations of integrated flap valve and holdfast base elements of nasal devices as described herein. For example.
Figure 5B:
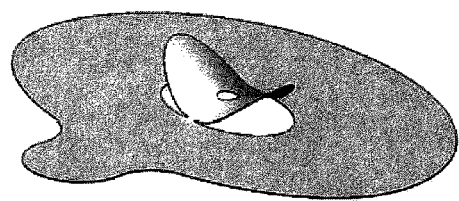
Figure 5C:
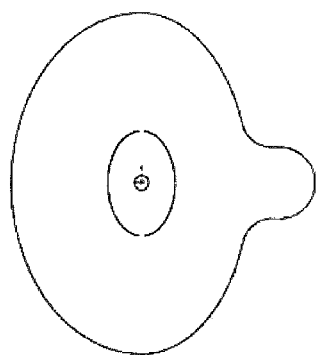
FIG. 5C shows a top view of a layer forming a holdfast base and a flap of an airflow resistor and FIG. 5D shows a side perspective view of the layer shown in FIG. 5C, including pseudo-color indicating stresses on the layer.
Figure 5D:
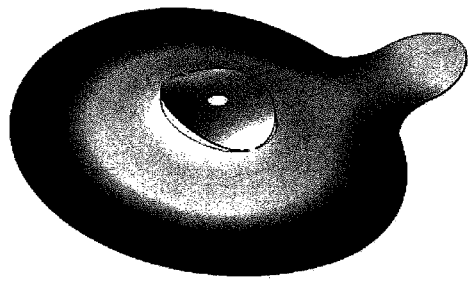

Any appropriate flap valve configuration may be used with the integrated holdfast/flap variations shown herein. For example, FIGS. 5A-5O illustrate different variations of flap designs. In FIGS. 5A and 5B, two flaps are cut into the integrated holdfast/flap layer, forming two flaps having a combined oval outline, with the flaps configured to open across the short axis of the oval, as shown in FIG. 5B. This variation also includes a leak path in the center of the valved region. Similarly, FIGS. 5C and 5D shows two flaps cut into an oval shape; however the flaps are configured to open across the long axis of the oval, as shown in FIG. 5D. In this variation.

Figure 5E:
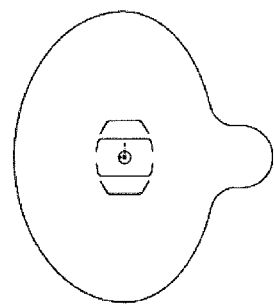
FIG. 5E shows a top view of a layer forming a holdfast base and a flap of an airflow resistor and FIG. 5F shows a cross-sectional side view through a nasal device incorporating the layer shown in FIG. 5E.
Figure 5F:
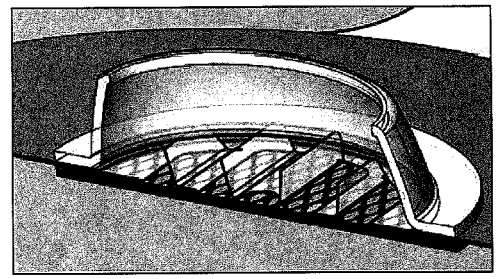
Figure 5G:
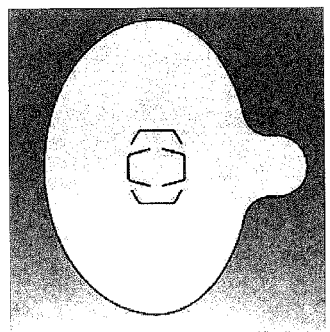
FIG. 5G shows a top view of a layer forming a holdfast base and a flap of an airflow resistor and FIG. 5H shows a side perspective view of the layer shown in FIG. 5G.
Figure 5H:
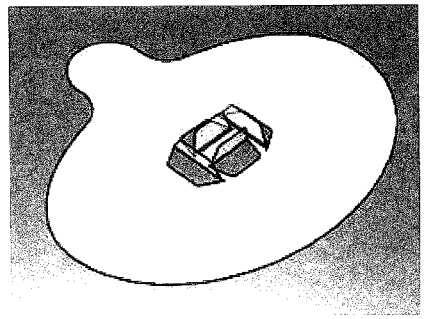
Figure 5I:
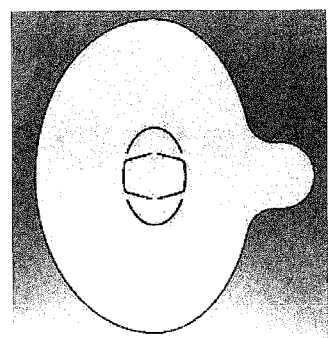
FIG. 5I shows a top view of a layer forming a holdfast base and a flap of an airflow resistor and FIG. 5J shows a side perspective view of the layer shown in FIG. 5I.
Figure 5J:
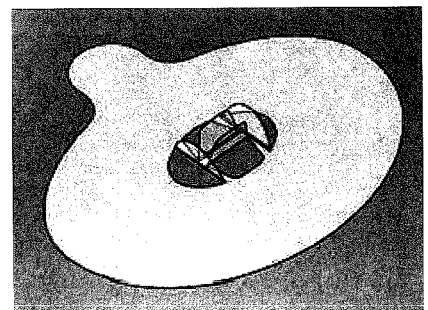

FIGS. 5E and 5F illustrate a variation having four cut-out regions forming four rectangular flaps, as illustrated in the cross-sectional view of FIG. 5F. FIG. 5G and illustrate another variation having four flaps that are approximately trapezoidal. FIGS. 5I and 5J illustrate a flap design that combines semicircular and trapezoidal flaps. FIG. 5J is a variation of a flap valve having two trapezoidal flaps extending across the long axis of the airflow resistor. FIGS. 5L and 5M show a variation of an airflow resistor having triangular flaps that open from a central point. Finally, FIGS. 5N and 5O show a variation having three flaps formed by somewhat rectangular or trapezoidal shapes having rounded edges.

The various flap designs illustrated herein (including those of FIGS. 5A-5O) may result in different noise levels during operation. Embodiments having rounded or curved edges may have noise-reduction properties compared to more sharp (e.g., angular) shapes. For example, compare the flap shapes of FIGS. 5E and 5F which have trapezoidal or rectangular shaped flaps with corners that meet at an angle to the flap shapes shown in FIGS. 5N and 5O which also have rectangular or trapezoidal flap shapes, but have rounded or curved edges. The flaps having rounded or curved edges may have a lower noise compared to otherwise identical flaps.

Figure 15A:
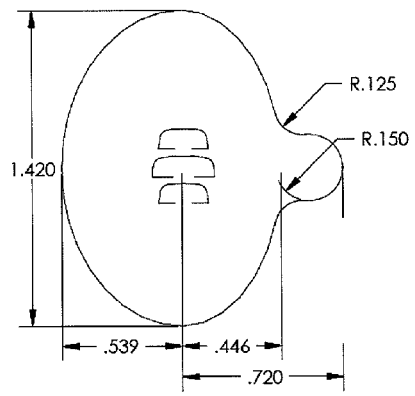
FIGS. 15A-15D illustrate variations of flap vales cut from the combined layer forming the flap valve portion of the airflow resistor and the base of the adhesive holdfast.
Figure 15B:
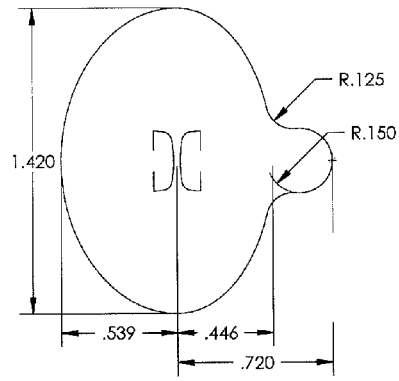
Figure 15C:
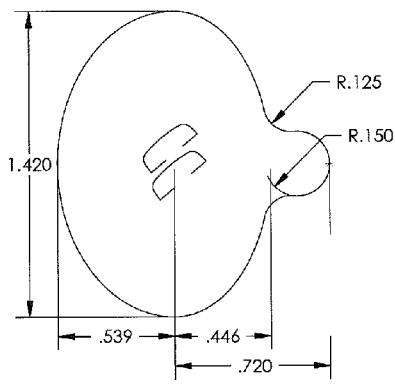

FIGS. 15A-15D show other variations of combined flap/holdfast layers that may be used. For example, in FIG. 15A, the flap valves include three parallel "fish scale" type flaps similar to those illustrated above; the flaps are oriented across the short axis of the device. FIG. 15B shows a similar variation in which the flaps are formed oriented across the long axis of the device; this variation includes two facing D-shapes. As an alternative, FIG. 15C illustrates a variation in which the flap valves are oriented at an angle (e.g., a 45° angle) with respect to the long axis of the device. Variations such as this may provide benefits in tolerances and performance depending upon the method of fabrication for the devices. This may be particularly true in variations in which the devices are formed at an angle on the backer cards, as shown in FIGS. 1E and 14. The flap openings may be angled equivalently to the angle that the devices are positioned on the backer card.

Figure 5K:
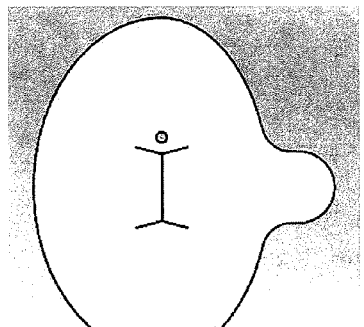
FIG. 5K shows a top view of a layer forming a holdfast base and a flap of an airflow resistor.
Figure 5L:
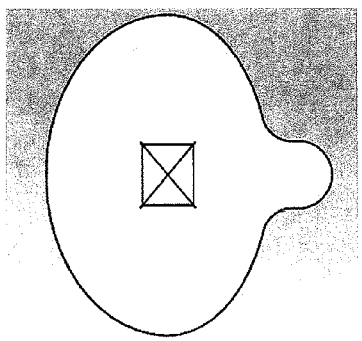
FIG. 5L shows a top view of a layer forming a holdfast base and a flap of an airflow resistor and FIG. 5M shows a side perspective view of the layer shown in FIG. 5L.
Figure 5M:
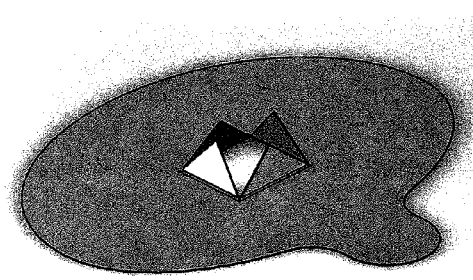
Figure 5N:
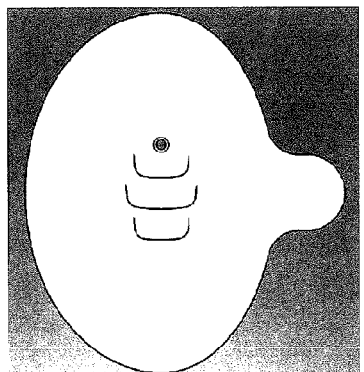
Figure 5O:
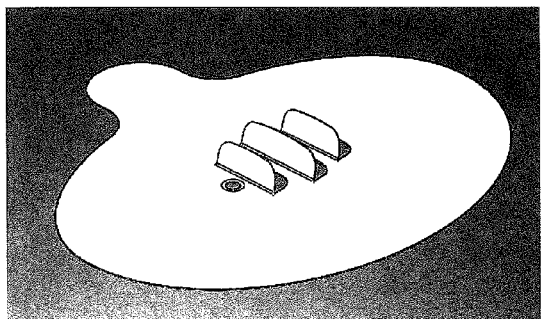
Figure 15D:
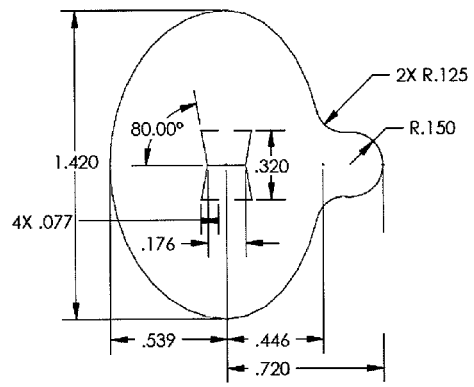
Figure 16A:
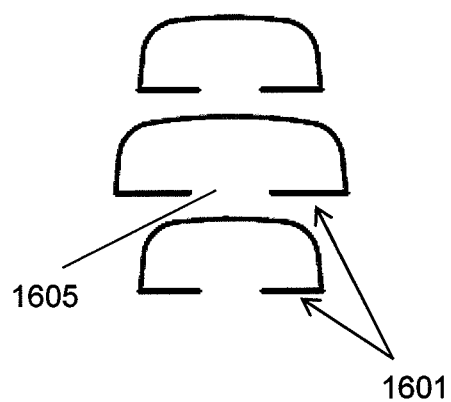
FIGS. 16A-16C illustrate features of various flap valves as described, including forming a narrower neck region on the flap by notching the flap, as well as flaps formed with rounded edges.
Figure 16B:
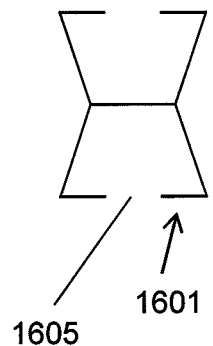
Figure 16C:
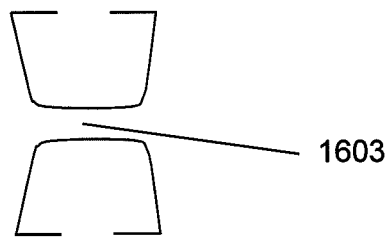

FIG. 15D shows another variation of a flap valve cut from into a flap/holdfast layer similar to the variation shown in FIG. 5K, but oriented along the short axis of the layer (e.g., so that the flaps open/close in the direction of the short axis). All of the variations shown in FIGS. 15A-15D include a cut-in region at the base of each flap. This is illustrated in greater detail FIGS. 16A-C. In FIG. 16A, which shows an enlarged view of the flaps cut into the layer shown in FIG. 15A, each of the three flaps includes a neck region 1605 formed by the two cut-in regions 1601. This neck region 1503 is therefore narrower than the length of the flap, and may therefore allow the flap to open with less resistance than it would have if the neck were larger. This, in turn, may help keep the resistance to inhalation (inspiratory resistance) low. The pattern of flaps shown in FIG. 16B illustrates one variation in which the flaps are formed immediately adjacent to each other, so that they share a common edge between them. FIG. 16C shows a similar variation, however the two flaps are separated by a space 1603. In this variation, when the flap is opened, the bridge of material between the two flaps will remain. Depending upon the fabrication method used, it may be beneficial to have each flap cut separately (e.g., not sharing edges), to prevent failure of multiple flaps if the process of cutting out the flaps fails. However, in some variations, it may be beneficial to share edges/cuts in forming the flaps because fewer cuts may reduce the overall chance that a cut will be unsuccessful.

Figure 6A:
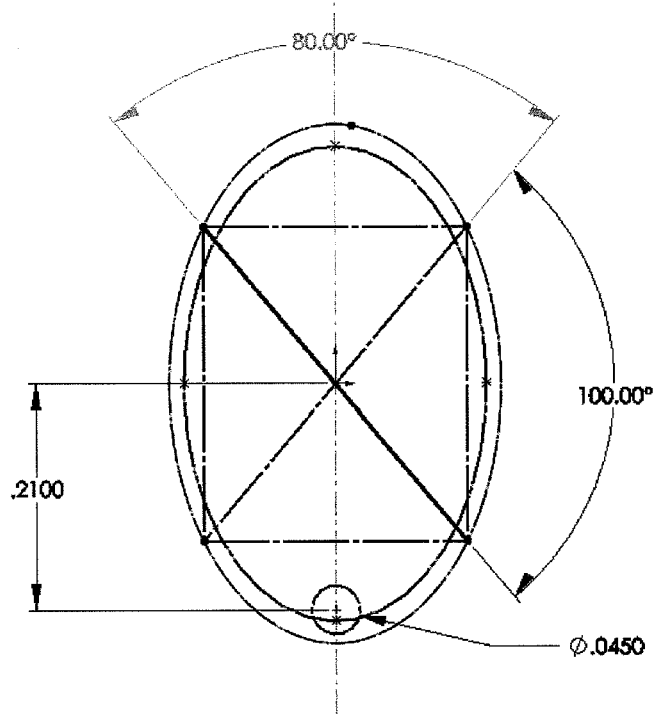
FIG. 6A shows a schematic view of another variation of a flap portion of an integrated layer of a nasal device.
Figures 6B, 6C:
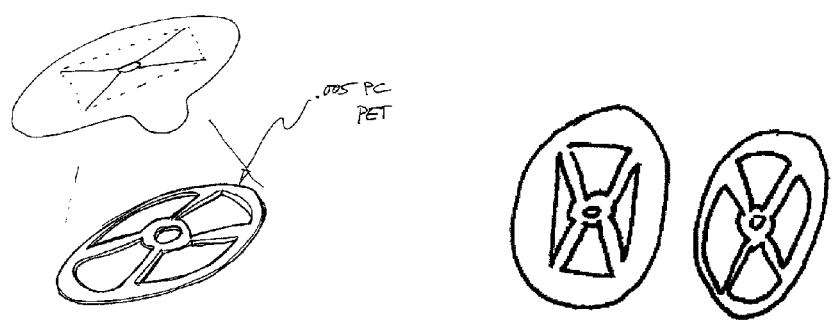
FIG. 6B shows an exploded perspective view (not to scale) of the layer shown in FIG. 6A with a valve limiting layer.
FIG. 6C shows different variations of the valve limiting layer of FIG. 6B.

In many of the variations described herein, the airflow resistor includes a flap limiting layer that is formed of a mesh. In some variations, the flap limiting layer is formed of a frame or sealing surface, against which the flaps rest when closed. For example, FIG. 6A illustrates a variation of a flap valve formed in an integrated holdfast/flap layer (similar to the variation shown in FIGS. 5L and 5M), that has four triangular shaped flaps. FIG. 6B shows this variation of a flap combined with a sealing surface to form an airflow resistor. In this example, the sealing surface is formed of a PET or polycarbonate frame having cut outs. The flaps seat against the sealing surface when closed. Any appropriate design of the seating/seating surface may be used, particularly those that allow seating of the flap edges against the surface when the flaps are closed. For example, FIG. 6C shows two variations of valve limiters that are configured for use with the pie-shaped flaps shown in FIG. 6A.

Figure 7A:
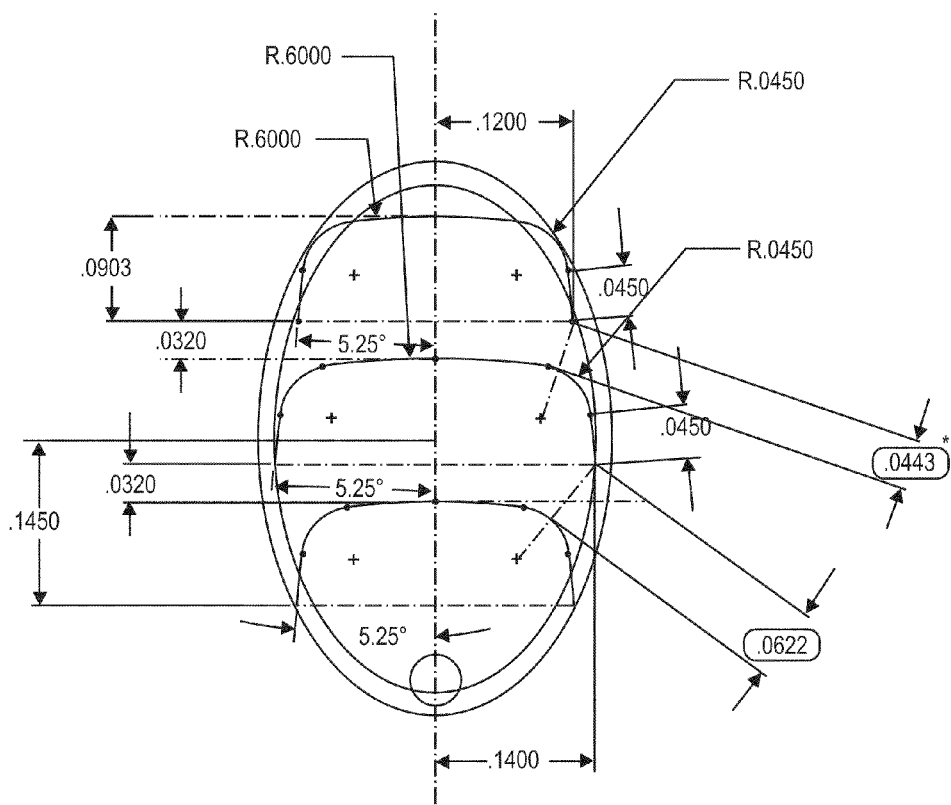
FIG. 7A shows a schematic view of another variation of a flap portion of an airflow resistor.
Figure 7B:
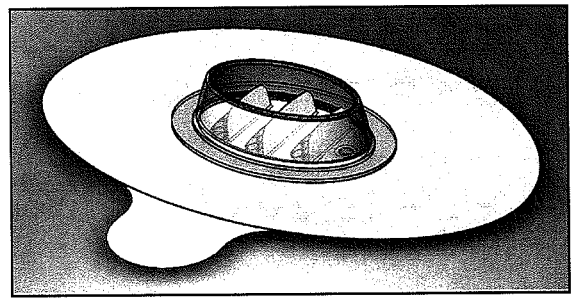
FIG. 7B shows a side perspective view of a variation of a nasal device incorporating the flap valve shown in FIG. 7A.
Figure 8A:
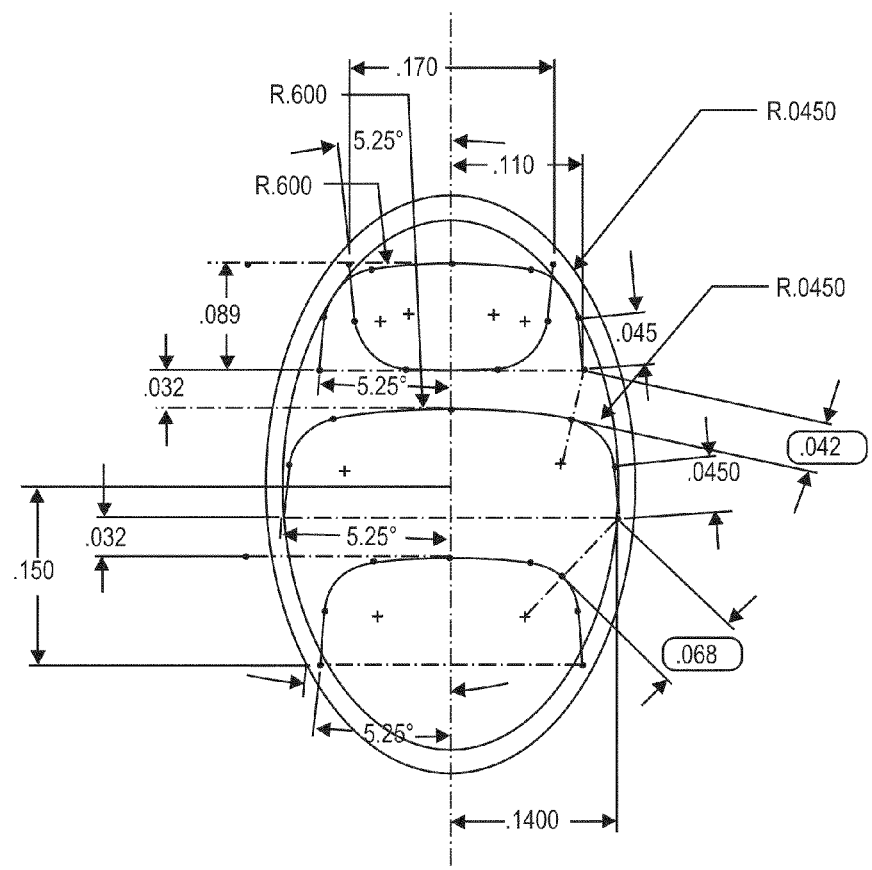
FIG. 8A shows a schematic view of another variation of a flap portion of an airflow resistor.
Figure 8B:
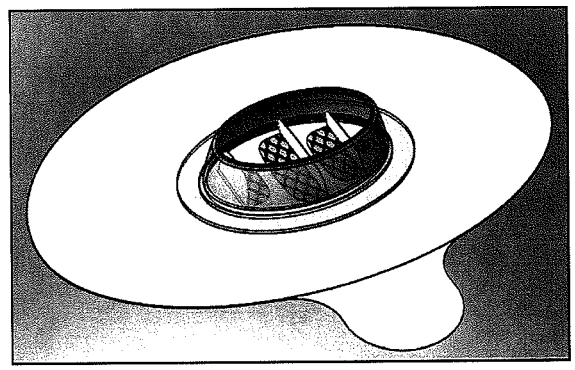
FIG. 8B shows a side perspective view of a variation of a nasal device incorporating the flap valve shown in FIG. 8A.

As mentioned, above, the variation shown in FIGS. 7A and 7B includes flaps that have rounded edges. In operation, these flaps, perhaps because of the gradually rounded edges, are less noisy (e.g., less prone to vibration) than similar flaps having more angular edges. Thus, in some variations, the nasal devices my include a noise-reduction feature that includes the shape of the flap valve. In particular, the noise-reduction feature may be the rounded edges of the flap, as illustrated in FIGS. 7A and 7B. An alternative view is shown in FIGS. 8A and 8B, in which the flaps are arranged so that the outer flaps in the oval profile open inwards (towards the center of the airflow resistor.

The aspect ratio of the flap may also be chosen to reduce device noise. For example, flaps that are wider than they are tong, (but not too wide) may provide more resistance. For example, aspect ratios (length:width) of between about 1.2:1 to about 3:1 may be noise reducing. Although flaps having aspect ratios closer to 1:1 may provide airflow resistors with lower inspiratory resistances, this aspect ratio may be slightly noisier (e.g., producing a buzzing noise). Increasing the aspect ratio may lower the noise, but may increase the resistance to inhalation.

A nasal device may also include (or alternatively include) other noise-reduction elements, as described herein. For example, the nasal device may include a projection or surface against which the flaps (and particularly the tips or outer edges of the flaps) may rest when they are opened (e.g., during inhalation). In some variations, the nasal device includes a projection extending across or partially over the airflow resistor on the side of the flap valve so that when the valve is open the outer edges of the flap valve contacts the projection.

Figure 10A:
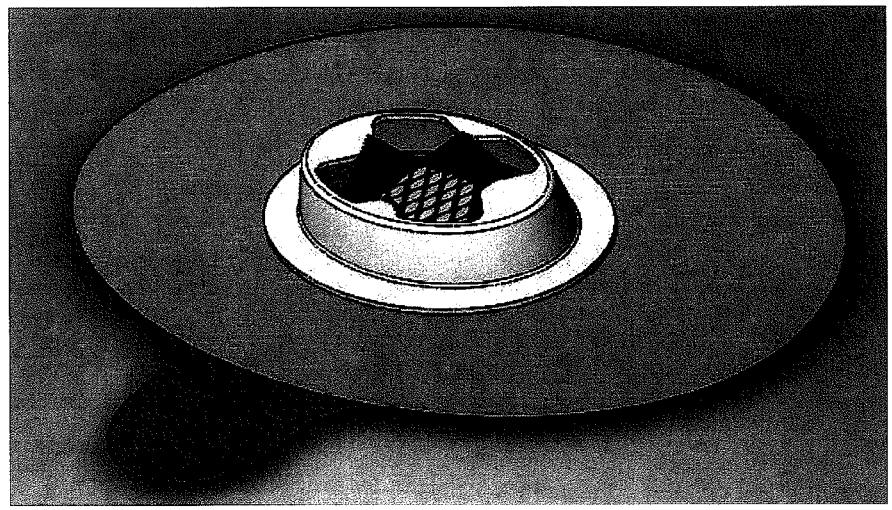
FIGS. 10A and 10B illustrate different variations of nasal devices.
Figure 10B:
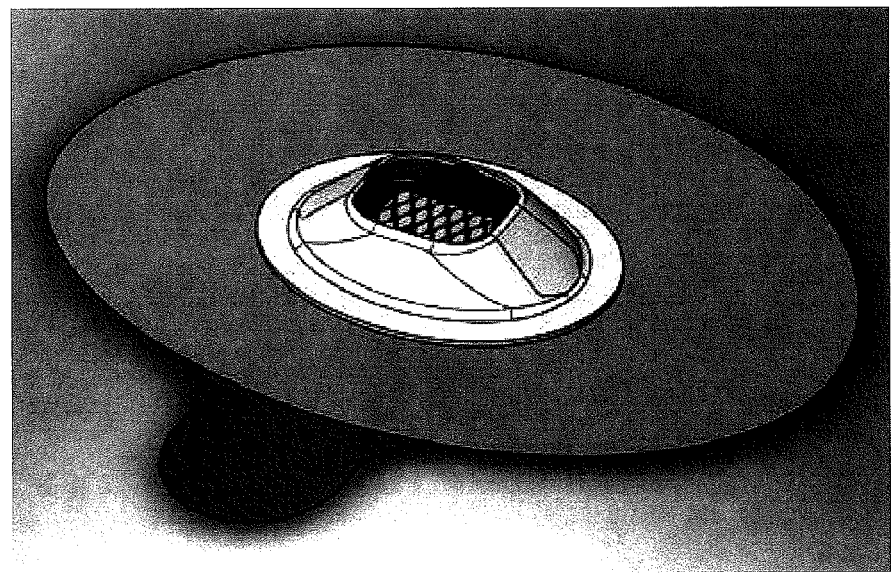
Figure 11:
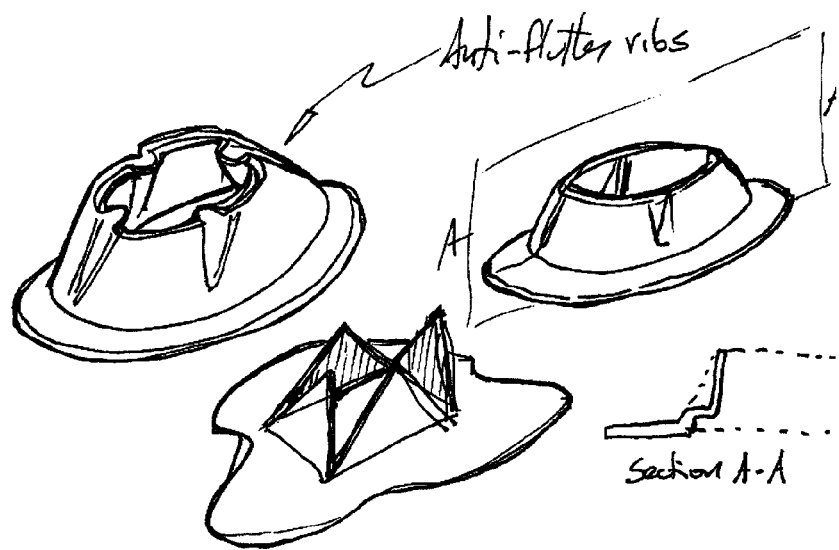
FIG. 11 illustrates different variations of rim body portions of nasal devices configured to limit noise.

FIGS. 10A-11 illustrate variations of the upper rim body (the flap cone) in which the walls of the rim body are adapted to contact at least a portion of the flaps when they are opened during inhalation, which may reduce the noise of the device. In FIG. 10A the cone includes projections partially across the upper surface. In FIG. 10B, the walls of the cone are tapered so that the flap contacts the walls when the flaps are opened during inhalation. FIG. 11 shows three variations of cones including one or more projections or valve-contacting surfaces that may reduce the nose through the device.

Figure 9A:
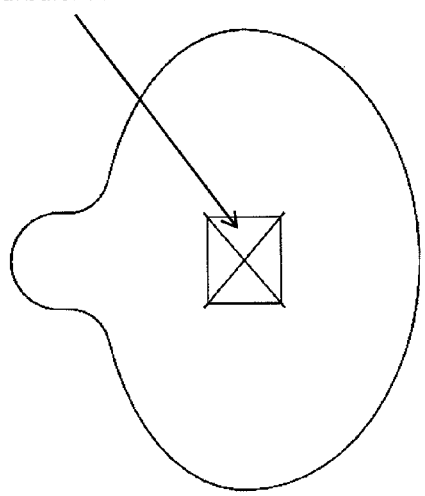
FIG. 9A shows a top view of another variation of a flap portion of an airflow resistor.
Figure 9B:
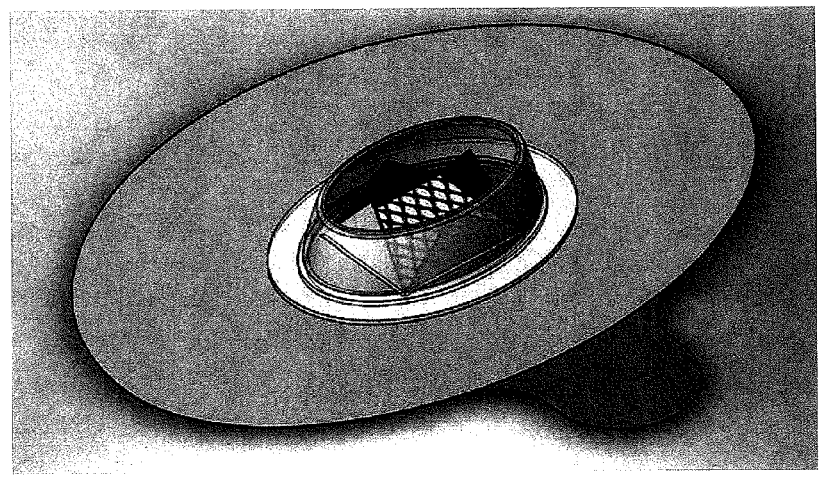
FIG. 9B shows a side perspective view of a variation of a nasal device incorporating the flap valve shown in FIG. 9A.
Figure 12:
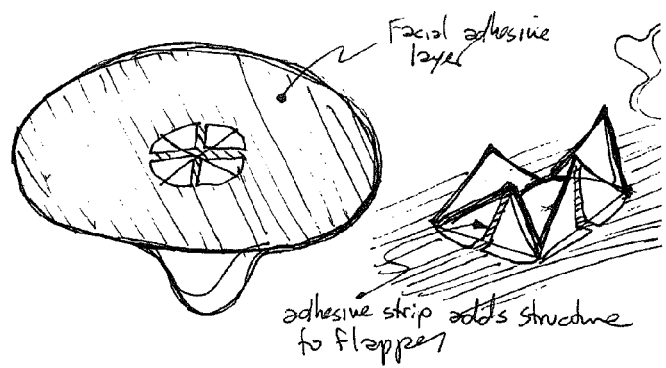
FIG. 12 shows top and side perspective views of another variation of a nasal device having a noise-limiting feature.

Other noise-reduction elements may include stiffeners along one or more regions of the nasal device (preferably not affecting the hinge region of the flap). Similar to the observations made above on aspect ratio, stiffer portions of the flap may help dampen noise-producing vibrations, while potentially increasing opening resistance (e.g., resistance during inhalation). In some variations a noise-reducing feature includes a stiffening or thickening region on the flap, preferably along or extending to an outer edge of the flap. Thus, the airflow resistor may include a region of localized thickness on the flap valves. FIGS. 9A and 9B illustrate a variation include a noise reducing feature on the flap valves. In FIG. 9A, a portion of the flaps are thickened by the addition of an extra layer on the flaps. This additional thickness may help stabilize the flap in turbulent airflow. The extra thickness region may be an adhesively applied layer (or may be simply an adhesive). FIG. 12 illustrates another variation in which a region of the flap is selectively thickened by strip of material that extends across the length of the flap to the edge. In this example, the flap is an adhesive strip that extends across the flap from the holdfast region.

As mentioned briefly above, any of the variations of nasal devices described herein may also be configured as PEEP-type nasal device. Thus, the nasal devices may be configured to increase the airflow through the nasal device when the pressure seen by the airflow resistor exceeds a threshold value. Normally the valve is closed during exhalation, and airflow through the nasal device (and thus the nostril(s)) is limited to airflow passing through the leak pathways. In some variations, the airflow resistor is configured so that the flaps may open slightly during exhalation above a threshold pressure.

Thus, in some variations the flap limiter (which may be a mesh or the like) is configured to allow the valve to deform in the direction of expiratory airflow when the pressure generated exceeds a predefined threshold pressure such as 1 cm $H_2O$, 2 cm $H_2O$, 3 cm $H_2O$, 4 cm $H_2O$, 5 cm $H_2O$, 6 cm $H_2O$, 7 cm $H_2O$, 8 cm $H_2O$, 9 cm $H_2O$, 10 cm $H_2O$, 11 cm $H_2O$, 12 cm $H_2O$, 13 cm $H_2O$, 14 cm $H_2O$, 15 cm $H_2O$, 16 cm $H_2O$, 17 cm $H_2O$, 18 cm $H_2O$, 19 cm $H_2O$ or 20 cm $H_2O$. In this manner, the valve may act like a threshold valve above a certain pressure, similar to PEEP valves that are used currently. Thus the valve may provide increasing pressure as flow rate through the valve increases, up until a point at which the pressure exceeds a threshold level and venting occurs. This my facilitate increased comfort and tolerability for the user and prevent excessive pressures being created which potentially could lead to expiratory mouth breathing. In some variations, as mentioned above, this may be accomplished by selecting a large enough pore size of the mesh or selecting a certain mesh pore geometry that allows the flap to deform in the direction of airflow during expiration (e.g., into the pores). Alternatively, in other embodiments of the flap limiter, the degree of overlap between the flap and the flap limiter may be reduced to promote buckling as expiratory pressures exceed a threshold level.

Figure 13A:
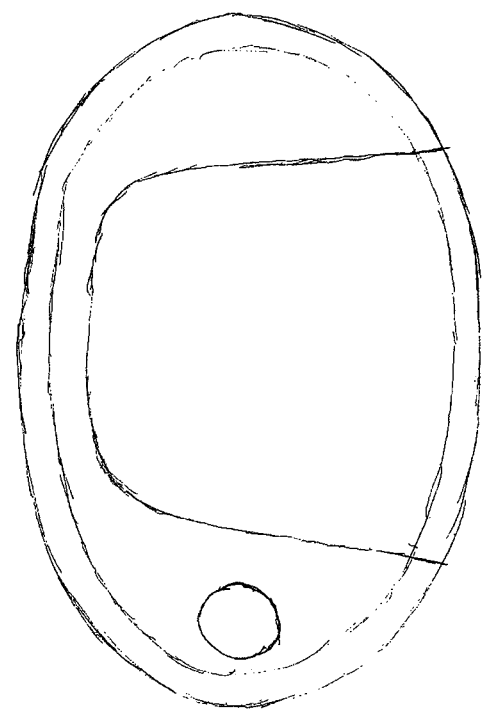
FIGS. 13A and 13B illustrate another variation of a flap valve and integrated flap valve/holdfast region for a nasal device as described herein.
Figure 13B:
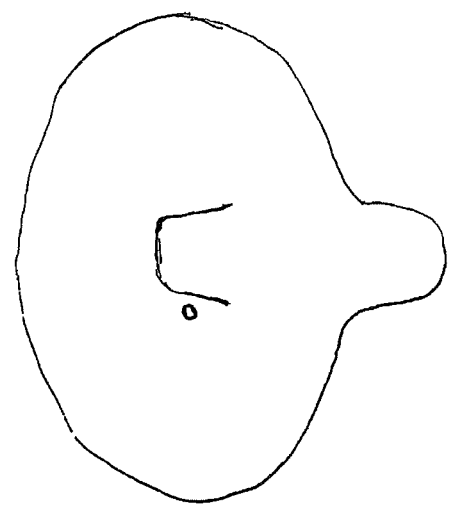

FIGS. 13A and 13B illustrate another variation of a region of a nasal device, in which the airflow resistor includes only a single flap valve. For example, FIG. 13A shows a portion of an airflow resistor (the outer oval shown is the footprint of the nasal cone as in FIG. 6A). The small circle is a leak pathway (expiratory hole), and the U-shape is the flapper cutout, forming a single flap valve. FIG. 13B illustrates an integrated flap/holdfast layer having a single flap valve. In FIG. 13B, the outer shape is the outline of the entire combined flap/holdfast layer as in FIGS. 5K and 5L. The U-shape is the flapper cutout.

The single-flap configuration may be particularly useful to preserve close to a 1:1 relationship of flapper length to width to minimize noise, while having rounded corners to further minimize noise. The single flapper configuration may help with the robustness of the device. For example, in some variations having multiple flaps forming the airflow resistor valve, the flaps man not all open during use. Under some conditions, after 1-2 flaps have opened, the pressure across the airflow resistor is reduced and there may not be enough pressure to cause the remaining flaps to open. This may result in a higher resistance due to smaller open surface area. With only one flap, the pressure will consistently ensure that the single flap opens and will then result in maximal open surface area every time. Also, the single-flap geometry may allows some flexibility for variation in placement of the nose positioning cone over the flapper cutout without interfering with the ability for the flapper to open while not giving up much potential surface area.

Monitoring Compliance

In general, the devices, systems and methods described herein are for determining or confirming that a nasal respiratory device has been worn and/or used by a subject. In particular, the devices, systems, and methods described herein may be used to determine compliance (e.g., application and/or use) of a passive nasal respiratory device, including those having an airflow resistor that is configured to inhibit exhalation more than inhalation and a holdfast configured to secure the nasal device in communication with the subject's nose (e.g., one or both nostrils and/or nasal passages).

Figure 17A:
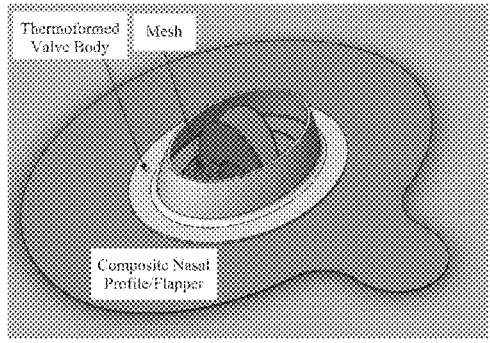
FIGS. 17A-17C show two variations of nasal devices.

Any appropriate nasal device may be used, including (but not limited to) those incorporated by reference above, and those illustrated in FIGS. 17A-18C. For example, FIG. 17A shows a nasal respiratory device configured to be secured to a subject in communication with a single nostril. The nasal device shown in FIGS. 17A-17C includes a central opening that is valved by an airflow resistor. The airflow resistors shown in FIGS. 17A and 17C are both variations of a flap valves. The flap valve in both examples includes a flap portion that is flexible, and is configured to open during inhalation and close against a valve limiting layer during exhalation. In FIGS. 17A-17C, the valve limiting layer is a mesh layer that is adjacent to the flexible flap valve and prevents or limits the valve from opening during inhalation. A rim body (also referred to as a valve body) surrounds the airflow resistor(s) in these examples. The rim body is on the side of the nasal device that faces the subject when the device is worn, and may be inserted at least partially into the nostril when the device is secured to the nose. The rim body may be adhesively secured around the airflow resistor by securing to the same adhesive that can be used to secure the device in communication with the subject's nasal cavity. A holdfast region surrounds the airflow resistor in these examples, and is configured as an adhesive layer that is initially in the same plane as the airflow resistor. An adhesive on this holdfast may secure the nasal device in communication with the subject's nose or nasal opening. The holdfast may flexibly conform to the surface of the nose, and may form a seat around the nostril or nostrils, so that airflow through the nostril(s) must pass through the nasal device(s).

Figure 17B:
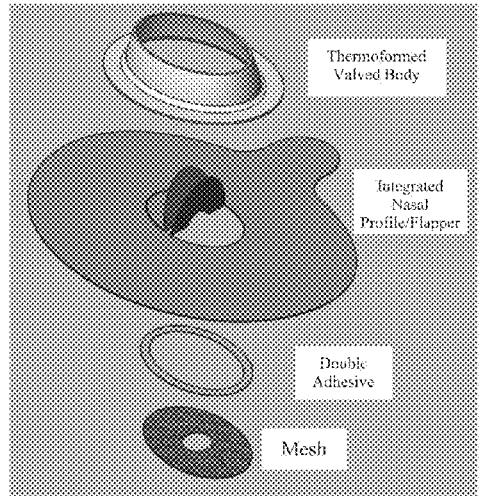

FIG. 17B is an exploded view of the nasal device shown in FIG. 17A, illustrating how the different components (flap valve and holdfast, rim body, and valve limiting mesh) all connect and interact. The nasal device may also include an adhesive connected to the holdfast ("nasal profile" region in FIG. 17B). The adhesive may have a thickness and provide support to the holdfast as well as making it adhesive to the subject's skin via a biocompatible adhesive. The nasal device may also include a protective cover over the adhesive that may be removed (e.g., a wax paper covering) before application. In some variations, as describe in greater detail below, the nasal device may include one or more sensors for determining compliance (e.g., use). For example, a sensor may be secured or in communication with the holdfast or the rim body of the nasal device. In some variations, the nasal device may include an indicator for indicating that the device has been applied and/or used by the subject. For example, the nasal device may be adapted to indicate that that the device has been worn. Also described in greater detail below, the nasal device may include compliance by changing color, or by otherwise providing an indicator or marker for use. In some variations, the adhesive of the holdfast may react when placed in contact with air, or with the subject's skin, or both, and provide a detectable (and in some cases quantifiable) measure of use.

Figure 17C:
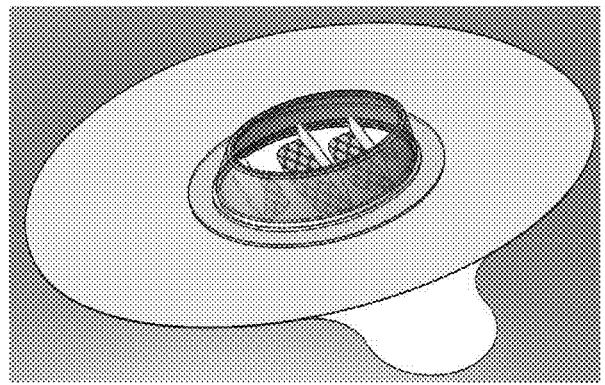
Figure 18A:
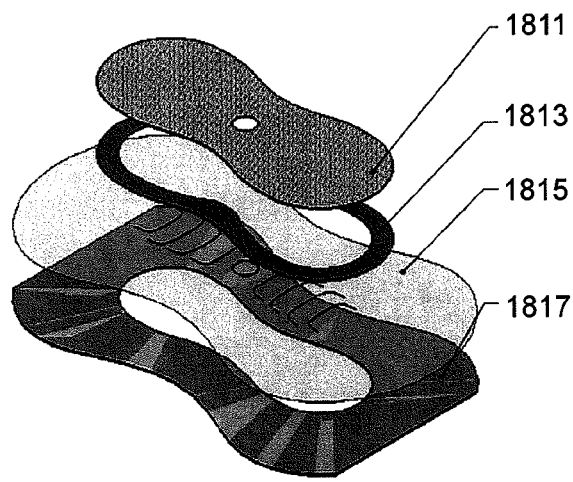
FIGS. 18A and 18B show two additional variations of nasal devices.
Figure 18B:
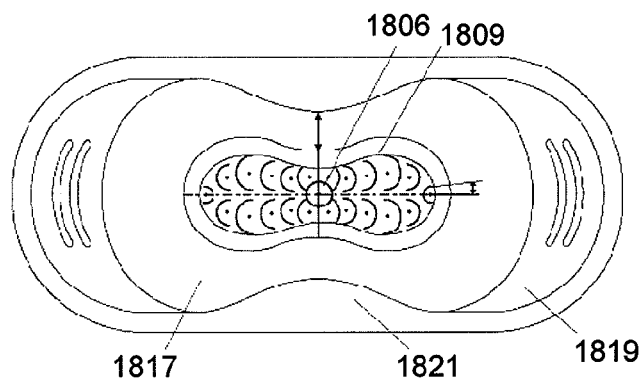
Figure 18C:
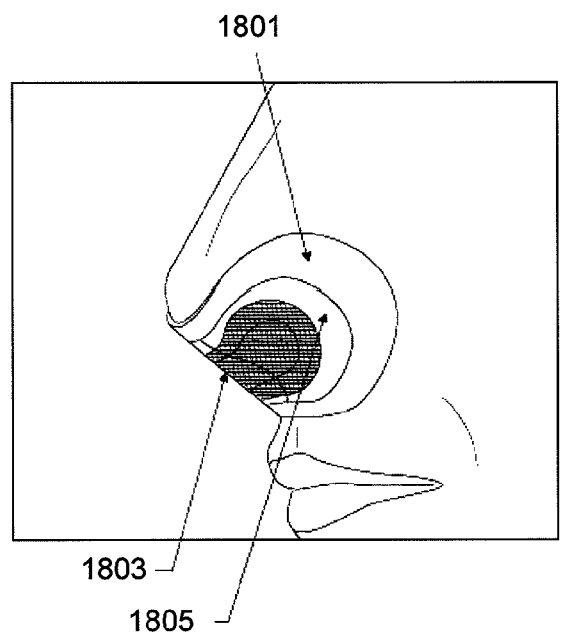
FIG. 18C illustrates the nasal device of FIG. 18A or 18B worn in communication with a subject's nose.

FIGS. 18A-18C illustrate another variation of a nasal device, configured in these examples as a whole-nose nasal device. Similar to the nasal devices shown in FIGS. 17A-17C, these nasal devices include an airflow resistor 1803 configured to inhibit exhalation more than inhalation, and a holdfast 1801. In FIGS. 18A-18C the holdfast is configured to secure the nasal device in communication with both nostrils (nasal passages). The variation shown in FIGS. 18A-18C does not include the optional rim body extending out of the plane of the device as shown in FIG. 17A-17C.

In the exploded view shown in FIG. 18A, the device including a central opening 1806 through the holdfast region 1817, 1819, 1821 (adhesive holdfast region across which an airflow resistor 1809 comprising a flap valve 1815 and a (mesh) valve limiting layer 1811 extend. The device may be applied and worn in communication with a subject's nasal passages as shown in FIG. 18C. As mentioned above, any of these examples may also include a sensor coupled to the device to determine or confirm that the subject has worn and/or used the device. In some variations the device includes an indicator that indicates that the device has been worn (or is being worn).

Figure 19:
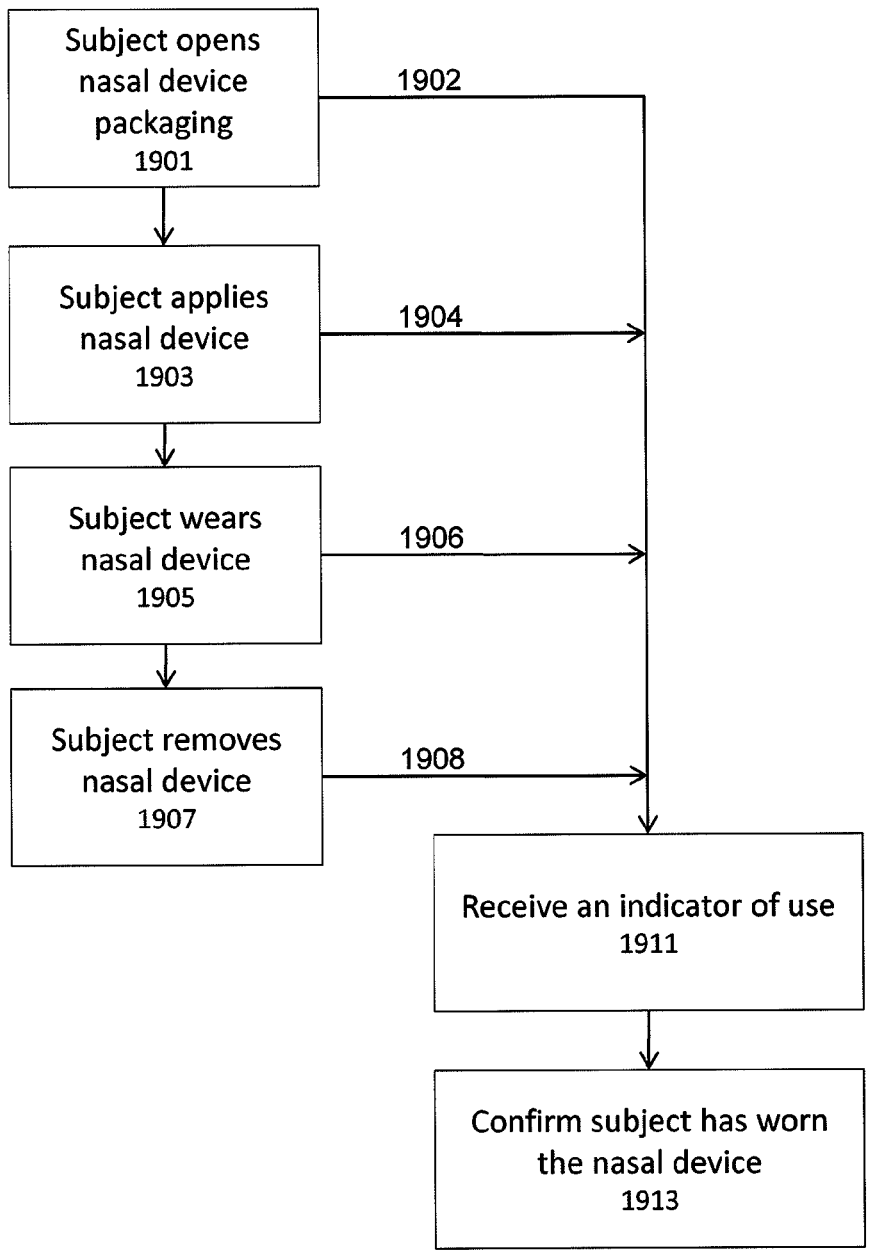
FIG. 19 is a diagram illustrating methods of confirming if a subject has worn a nasal device.

In operation, the devices and systems described herein may be used to determine and indicate if a subject has worn one of the nasal devices. FIG. 19 is a flow diagram illustrating some of the methods for determining compliance as described.

The diagram shown in FIG. 19 illustrates different variations of methods by which the compliance (or use) of a nasal device may be determined and/or monitored. In operation, the user of the medical device typically applies the nasal device in communication with their nasal cavity (e.g., one or both nostrils) 1903.

If the nasal device is initially provided in a packaging, i.e., a sterile packaging, the nasal device may first be removed from the packaging, 1901. In some variations, use may of the nasal device may be monitored or confirmed at this stage (arrow 1902), either automatically or by the subject using the device. For example, the device packaging may include a marking or code that is on or in the packaging, including on the inside of the packaging. For example, when the subject opens the packaging, it may reveal a code or marking (including an alphanumeric marking) that the subject can report to indicate use of the device. The subject may be directed to call a number and enter the code, or log into to a website to enter the codes, or enter the code in a tracking device that they are provided. In some variations, the subject may record the code in a log. In variations in which the code is entered by computer or by telephone (calling, text messaging, etc.), the entry may be date and time stamped, and this information may be recorded in a remote or central database for later review and confirmation.

In some variations, the device may be dispensed from a dispenser, which may be configured to record use. For example, a dispenser may record or track use of the device. A dispenser may be configured to store use information (for later collection or uploading/sending to a processor or processing center) or it may be configured to communicate directly with a processor or processing center.

In some variations, the subject may provide the used packaging (and/or the used device, as described below), for tracking, confirming or monitoring use. The subject may be provided with a postage-paid return package, for example. In one variation the packaging or dispenser for holding the new devices may be convertible into a return/collection package that may be used to store the used devices or packaging for mailing to a processing center where the use may be determined or confirmed. In some variations, a collection device may be provided to the subject to receive the use packaging and/or devices.

Figure 20A:
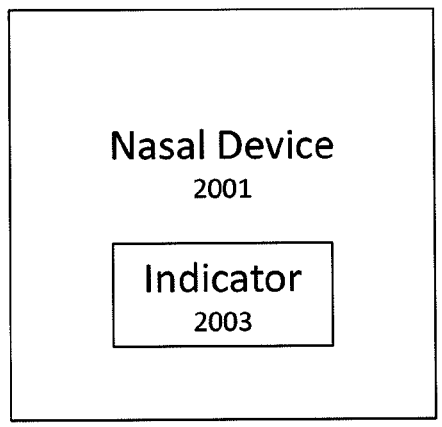
FIGS. 20A and 20B schematically illustrate nasal device configured to monitor and/or confirm usage of the nasal device by a subject.

In the examples described above, the packaging or a marker/code on the packaging acts as an indicator of use of the nasal device. For example, FIG. 20A schematically illustrates a nasal device having an indicator. An indicator of use may be received by a processor or analyzer (which may include a processor) for tracking or determining/confirming that the subject has been using the nasal devices. In any of the variations described herein, the subject may be identified (either by name, code, or anonymously), so that the use can be correlated to a particular subject. This may be performed in a manner that protects subject confidentiality, or it may identify the subject.

The processor or analyzer may receive regular use information, or it may receive information in discrete packets of information 1911. For example, the processor may receive information regarding use as the subject uses the devices (e.g., when the subject sends or logs each use), or the processor/analyzer may receive updates weekly, monthly, etc.).

The processor or analyzer may then confirm, by examining the use data from the received indictors of use, that the subject has been complying with treating and regularly using the devices 1913. An analyzer/processor may be software, firmware, or hardware that is configured to receive, tabulate, analyze and/or provide output on the use or compliance of one or a plurality of subjects using the device. For example, an analyzer/processor may include a computer or digital processor (e.g., a CPU, etc.) or it may be software configured to run on hardware. The analyzer/processor may be local or remote (e.g., a central server/processor). The analyzer/processor may also be configured to provide output on the use/compliance behavior of one or a plurality of subjects. For example, the analyzer may provide a printout, electronic copy, text message, or the like summarizing one or more subjects' use or compliance. The output may be in graphical, text and/or numeric format. In some variations, the analyzer may provide an index of compliance or use, for example, indicating that a subject use the device X % of the time. In some variations, the analyzer/processor may also be configured to provide information on the operation of the device. As described in some detail below, some of the indicators of use received by the analyzer may also be used to extract information about the functioning of the device worn by a subject. In other variations, information about the subject and the use of the device (including subject-reported feedback, etc.) may also be sent along with, or as part of the indicator of use. Any of this information may also be analyzed, displayed and/or saved by the analyzer. The data produced by the analyzer may be provided to a medical practitioner (e.g., physician, therapist, researcher, etc.) or a supervisor.

Returning now to FIG. 19, indicator of use information may be sent or provided once the subject applies the nasal device 1903, 1904. For example, a picture of the subject wearing the device (which may include a time/date stamp) may be provided as the indicator of use. In some variations, the subject is provided with a monitoring device that includes a camera to take a picture of the device once it has been applied. Another variation may include an application that may be used by a subject to monitor use. For example, the subject may use a computer application configured for a laptop, desktop, portable/handheld device mobile phone such as an iPhone™, iPad™, etc.) that may collect a photograph of the subject wearing the device. This visual indicator of use 1911 may be automatically or manually analyzed.

Figure 20B:
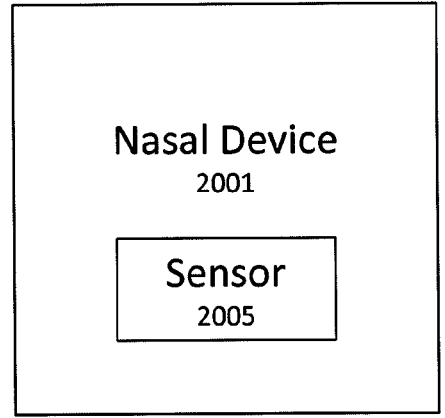
Figure 20C:
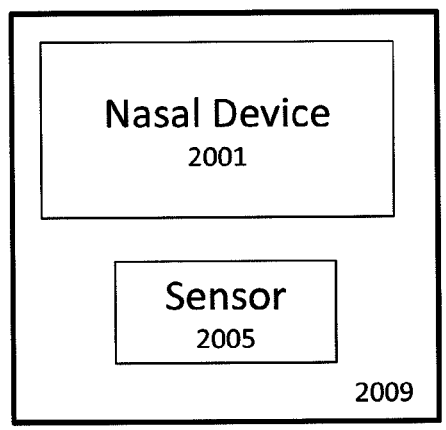
FIGS. 20C-20E schematically illustrate systems configured to monitor and/or confirm use of the nasal device by a subject.
Figure 20D:
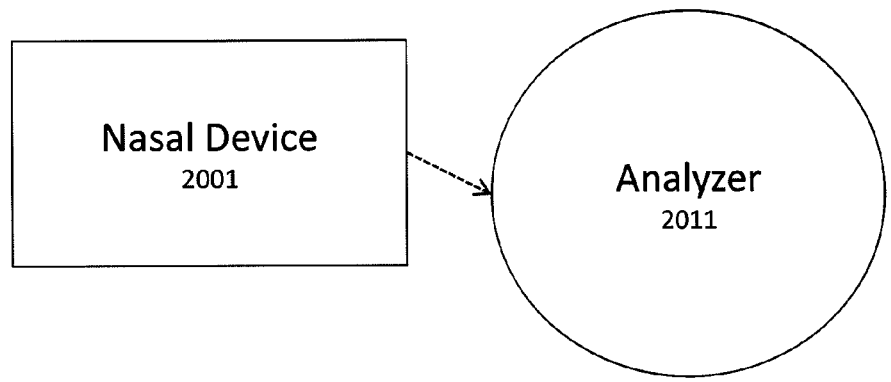

In some variations, the nasal device may be configured to reveal a code or other specific identifier once the device has been applied to the subject's nose. For example, a heat-activated ink or dye may be used to reveal a code that indicates that the device has been applied. Other examples may include markings that become visible upon reaction with skin oils, air, light, etc. The subject may then report this identifying information themselves or it may be automatically provided. For example, in some variations, after applying the nasal devices, the subject may (by looking in a mirror, or by taking a picture) provide the indicator of use information to a monitoring device or to a remote analyzer/processor. The subject may call, text, email, etc. to report this information. In some variations, the subject enters the information into a remote monitor.

in some variations, the nasal device includes one or more sensors to determine use of the nasal device. FIG. 20B schematically illustrates one variation of a device including a sensor, and FIG. 20C shows a system including a sensor for use with the nasal device. Any appropriate sensor may be used, including thermal (e.g., thermister), chemical (e.g., moisture), mechanical (e.g., strain), electrical (e.g., conductivity) or the like. The sensor may be configured to determine when the device is applied to the subject and may store this information, or it may send it (e.g., wirelessly) to a local or remote monitoring device. Thus, in some variations the devices may include a sensor and/or a memory or communication element (e.g., software/hardware/etc.).

In some variations, the use or compliance information is provided as the subject is wearing the device 1905, 1906. For example, the nasal device may include a sensor that is configured to detect use and continuously monitor operation of the device as it is worn. FIGS. 21A-22C illustrate examples of this type of variation.

As illustrated in FIG. 19, during operation of the nasal device, as the subject is wearing the device 1905, information from the sensor(s) may be sent to a monitor or analyzer/processor 1906 either continuously or periodically to track and/or monitor the usage. The sensor may be configured as part of a circuit that actively monitoring use or operation of the nasal device. For example, the sensor may detect body heat and determine that that the device is being worn by the subject, or it may detect flow (airflow) through the nasal device, or it may detect changes in respiration e.g., via thermister) as the device is worn. A sensor circuit may include a timer or clock that indicates when and/or for how long the device is being used/worn. In some variations the circuit may store this information. The circuit may include a memory or data storage element, as mentioned. The circuit may also include logic to confirm that the signals received by the sensor (s) are expected for use of the nasal device by a subject. The circuit may include a power source (e.g., battery, capacitor, etc.), or an external power source may be used. The circuit elements including the sensor may be integrated in or on the nasal device, or they may be separate from the nasal device, as part of a system for monitoring.

In some variations, information indicating the use of the nasal device may not be passed on to a monitor, analyzer or processor until after the device has been worn (e.g., overnight) and removed 1907, 1908. In some variations, the information about the use of the nasal device is extracted from the used nasal device. For example in some variations, the nasal device may include an indicator of use that reacts after application of the device to a subject's skin or over time white the subject is wearing the device. In particular, the holdfast region of a nasal device may be an adhesive holdfast. Application and wearing of the nasal device my alter the adhesive holdfast, or another portion of the nasal device, in a manner that can be detected by a monitor or analysis device. For example, stretching or mechanical deformation of a nasal device (e.g., the holdfast region of a nasal device) may occur when the device is worn, and this may be detected. For example, the material forming a portion of the holdfast may change color when deformed, and this color change may be optically detected. In some variations, the device may be examined for the presence of skin oil or the like (e.g., using an ultraviolet light source). In still other variations, the device may store (digitally) information on operation/use as mentioned above and this information may be downloaded.

As mentioned, FIG. 19 illustrates various embodiments of methods for using the nasal devices described herein. In some variations, more than one reporting/detection method and/or time of reporting (1902, 1904, 1906, 1908) may be used. For example, a monitor may be sent information both when the subject applies the nasal device (1903, 1904) and when the subject removes the nasal device (1907, 1908).

FIGS. 20A-20E show schematic variations of some of the embodiments mentioned above. For example, devices 2001 that include integrated indicators 2003 are illustrated schematically in FIG. 20A. Examples of this variation may include nasal devices having one or more indicator region on the device (e.g., on the holdfast, a body region, the airflow resistor, etc.) that indicate that the device is being worn or for how long the device is worn. For example, as mentioned above, the device may include an alphanumeric code printed that is revealed only after the device is worn for a certain number of hours. This code may be unique to the device worn. The subject can then enter the code into a database (e.g., an online database) to verify usage of the device.

FIG. 20B shows another schematic illustration of a nasal device 2001 including a sensor 2005. As mentioned above, the sensor may be a sensor such as a thermal sensor (e.g., thermister), chemical sensor (e.g., pH), mechanical sensor (e.g., strain), electrical sensor (e.g., conductivity, galvanic sensors, etc.) or the like. The sensor component 2005 may include circuitry to support activity of the sensor, including a power supply, data storage, clock, communications (e.g., wireless transmitter), or the like. The sensor and supporting components may be miniaturized. In some variations the sensor is coupled to the nasal device while the support elements are not, but are connect to the device and may be attached to it, and worn by the subject separately (e.g., clipped to clothing or attached to the body.

FIG. 20C illustrates a schematic of a system including a nasal device and a sensor at is not coupled to the device, as illustrated FIGS. 21A-22C, described below.

Any of the variations described herein may also include a monitor or analyzer for receiving and/or analyzing indicators of usage of a nasal device. In some variations, such as that illustrated schematically in FIG. 20D, the analyzer is a component that is separate from the nasal device but receives either information about the usage of the nasal device (e.g., a code from the nasal device, a picture of the nasal device being worn, or the like) or the actual used nasal device 2001. For example, the analyzer 2011 ma be a monitor that is operated or held by the subject to store or track usage data. This local analyzer or monitor (local to the subject) may communicate with a remote analyzer (remote from the subject) that may store, analyze and/or present the data. Alternatively, a remote analyzer alone is used as part of the system. For example, in some variations the analyzer is held and operated remotely, and the subject sends the packaging, the nasal device, information about the nasal device (e.g., codes, etc.) to a remote analyzer. Thus, a subject may mail the device or information about the subject and the device to a remote analyzer.

Figure 20E:
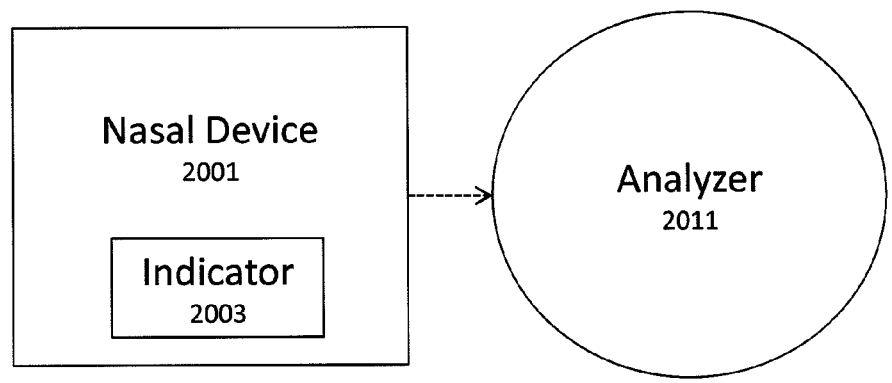

In one example, the nasal devices are examined and analyzed by a remote analyzer that uses ultraviolet light to confirm use. For example, the subject may be prescribed a course of nasal devices that include a 30-day supply of devices, the device may be sent with (or in) a box having storage compartments for the nasal device. If two nasal devices are worn per day (e.g., one for each nostril) then the subject may return both of them, or one of them. The subject is instructed to place the used nasal device into the separate compartments of the box, which secures them inside. The storage box can then be sent to the remote analyzer to confirm that they were worn. For example, a manual analysis of the nasal devices may be performed using a florescent light (e.g., a Wood's lamp) which will fluoresce because of the oil/sebum or presence of foreign particles such as tint or dirt on the adhesive where the device has been used. An unused device will not fluoresce. In some variations, as the nasal device may also include an indicator 2003 that may read or reviewed by the analyzer 2011, as shown in FIG. 20E.

Figure 21A:
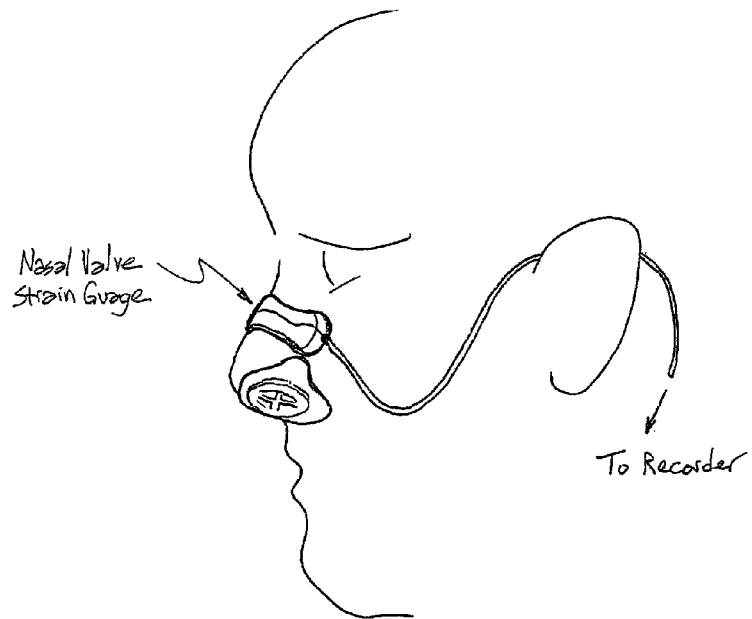
FIGS. 21A and 21B one variation of a system for confirming use of a nasal device.
Figure 21B:
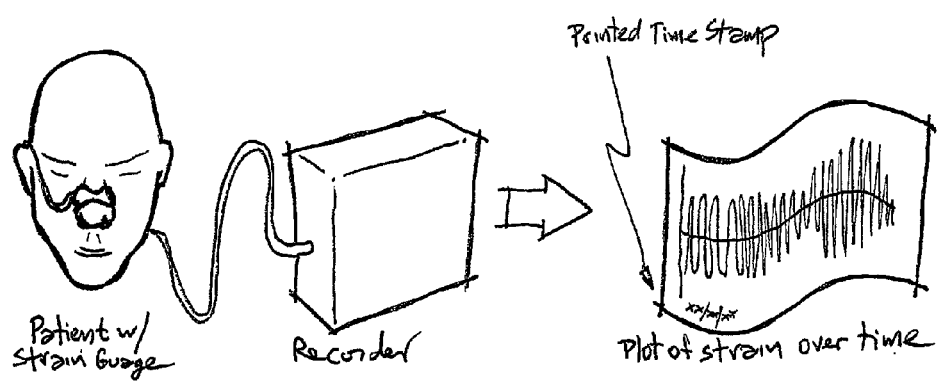

FIGS. 21A and 21B illustrate a system for confirming use of a nasal device that include a strain gauge to determine the movement of the nasal device (or the nose) during exhalation and inhalation. In FIG. 21A the nasal valve strain gauge is shown secured over the bridge of the subject's nose while they are wearing the nasal device(s) in communication with their nasal passages. The strain gauge (sensor) may communicate either wirelessly (not shown) or via dedicated connection to a monitor device, shown here as a recorder. In this example, the monitor device records the output of the strain gauge over time, showing the movement of the nose. In variations in which the strain gauge is separate from the nasal device, the same sensor may be used to confirm use and activity of many different nasal device (e.g., reused). The monitor or a analyzer) may be configured to review the data to distinguish between traces made when the nasal device is being worn (e.g., which may emphasize the nostril or device motion) and when a nasal device is not being worn. This is illustrated in FIG. 21B. In some variations, the strain gauge is integral to the nasal device. For example, the strain gauge may be coupled with or part of the adhesive holdfast region; breathing while wearing the device may be detected.

Figure 22A:
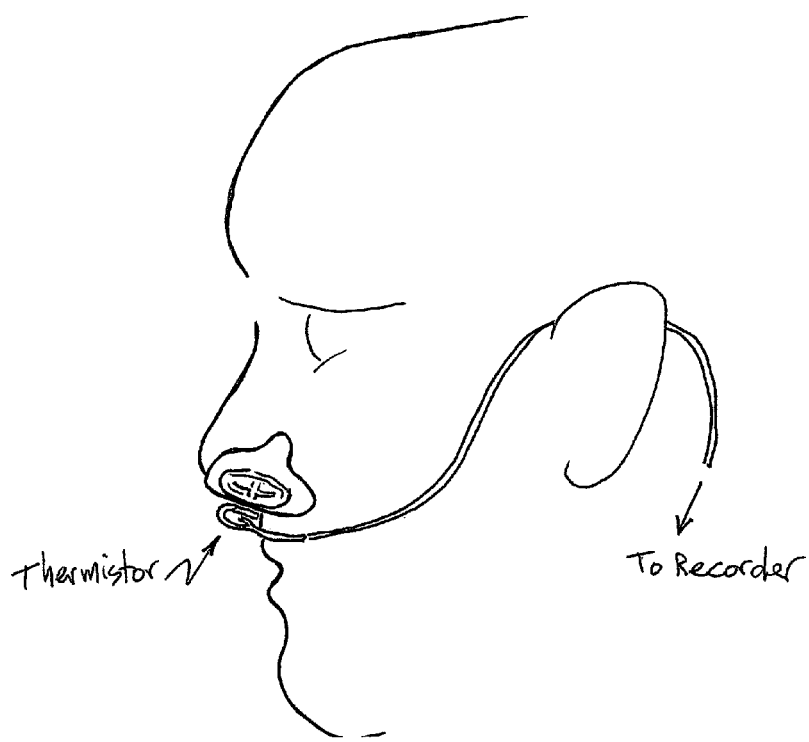
FIG. 22A-22C illustrate another variation of a system for confirming use of a nasal device.
Figure 22B:
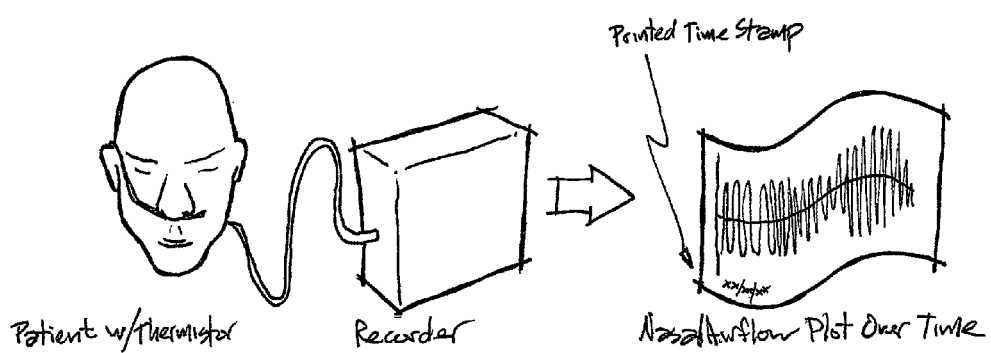
Figure 22C:
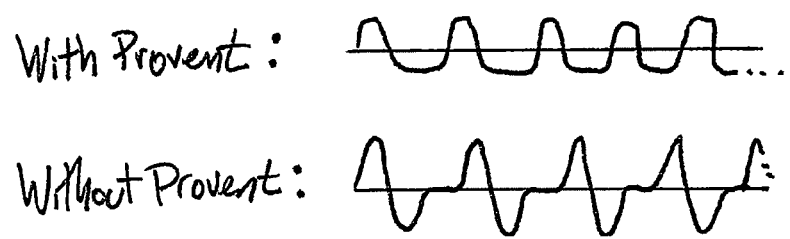

FIG. 22A shows a variation of a system including a thermister positioned outside of the passageway through the nasal device to detect flow through the nasal device. As just described, the sensor (thermister) may be integral to the device, or separate from the nasal device. In variations in which the nasal device is integral, the nasal device and sensor may be disposable. In some variations the sensor may be coupled or removably attached to the nasal device and re-used with different nasal device. Alternatively, the sensor element may be worn even without the nasal device. FIG. 22C compares examples of signals from the thermister when the nasal device is and is not being worn.

Other examples of nasal devices and systems to monitor use/compliance may include nasal devices that are packaged with or include tamper-evident labels or markers that indicate that the device or packaging has been manipulated. For example, the device may include one or more markers that indicate stretch/deformation of the device (e.g., the holdfast). In some variations the device may incorporate a pH/litmus type of chemical marker. The device may include a heat-activated dye or indicator on the device. Any of these indicators may also provide an estimate of how long the device was worn. For example the device may include a color change indicator that tells how long it was exposed to air, or in contact with skin.

in one variation, the device may include one or more component parts that swell or become swollen upon repeated exposure to humidity, particularly to the sustained or repeated exposure to nasal airflow, which typically contains water vapor. The swelling may be visible or non-visible. Swelling may be detected by including one or more markings on the device, or by gross changes in the shape or size of the device. The swelling may be detected by manually or automatically examining the device. In some variations, the exposure to humidity may result in a color change. In some variations, the device may react to the presence of moisture in ambient air; in some variations, the device may respond to the greater level of moisture in airflow through the nasal passage.

Another example includes the use of an adhesive layer (with a specially chosen thickness, application pattern and/or material) on a nasal device that when worn and subsequently no removed from the user's skin will visibly appear to "clump" or otherwise no longer remain smooth and flat.

In general the systems and methods may be used to monitor use. For example, the device may include a monitor to monitor operation of the device as it is worn. In one variation, the device may be use with a home monitor that is configured as a portable PSG (polysomnogram) to detect not only use of the device, but also the effect of the device. This information may also be conveyed to the monitor/analyzer for analysis. In one variation, the device may be used with a home pulse oximetery recorder to detect the operation of the device by the effect on blood oxygenation, and to provide additional data.

As mentioned above, the devices may be used with optical imaging elements providing evidence that the device was applied (using a time stamp to image the device after applying it, and before removing it). In some variations the device may include a novel marker that is imaged to both shown which device is being used, but also such a label could be on the outside to confirm the same device is being worn after applying it and before taking it off (e.g., in the evening and in the morning).

In some variations the nasal device may include an RFID detector/detection mechanism to uniquely identify the nasal device. In one variation the subject may wear or sleep near a monitor that detects (by RFID) the presence of the nasal device on the subject as it is worn.

Many of the variations described herein permit more or less subject-reporting (self-reporting). For example, the subject may simply log his own usage, or the logging may be performed automatically. Some of the variations described herein may be made tamper-resistant, so that the subject cannot "fake" wearing the device. For example, methods and systems that examine or receive feedback reflective of the sustained operation of the nasal device are difficult for a subject to fake.

In some variations the nasal device or a system including a nasal device tracks or monitors changes in the nasal device to confirm use. For example, in nasal devices include a flap valve, the system may examine changes in the flap valve that reflect changes due to the motion of the flap valve during operation. Stress on the flap valve may be detected; in some variations the flap valve may be coated or embedded or may otherwise include a stress-indicating compound. For example, a time-release coating may be used.

Some variations already mentioned above include monitoring of the activity of the device as it is worn, including the monitoring of respiration. In some variations, the activity of the nasal device as it is worn may be confirmed by the detection of the noise of the device the movement or closure/seating of the valve in the airflow resistor may be detected, etc.). In some variations the detector may be a sound detector, for detecting the movement of the valve. Thus, a microphone may be used as part of a monitoring device. Appendix A shows a visual mapping of many of these ideas, as well as others.

White the devices (and methods for using the) have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the invention.

What is claimed is:

1. A nasal device for inhibiting exhalation more than inhalation, the nasal device comprising:
   a flap/holdfast layer comprising a flap portion and a holdfast portion;
   a flap limiting layer adjacent to the flap portion, wherein the flap limiting layer and the flap portion form an airflow resistor configured to inhibit exhalation more than inhalation;
   an adhesive ring between the flap limiting layer and the flap/holdfast layer; and
   an aligner extending from at least one side of the flap/holdfast layer and at least partially surrounding the flap portion.

2. The device of claim 1, further comprising an adhesive material on the holdfast portion of the flap/holdfast layer.

3. The device of claim 2, wherein the adhesive material comprises a core layer having an adhesive on either side.

4. The device of claim 3, wherein the core layer comprises a fabric.

5. The device of claim 1, wherein the flap portion comprises multiple flaps cut from the flap/holdfast layer.

6. The device of claim 1, wherein the flap/holdfast layer further comprises one or more openings forming a leak pathway through the nasal device.

7. The device of claim 1, wherein further comprising a lower rim body extending from the opposite side of the flap/holdfast layer, away from the aligner.

8. The device of claim 1, wherein the aligner is adhesively secured to the flap/holdfast layer.

9. The device of claim 1, wherein the flap limiting layer comprises a mesh.

10. The device of claim 1, wherein the flap limiting layer comprises a frame.

11. The device of claim 1, further comprising a noise reduction feature.

12. The method of claim 1, wherein the flap/holdfast layer comprises urethane.

13. A nasal device for inhibiting exhalation more than inhalation, the nasal device comprising:
    a flap/holdfast layer comprising a flap portion and a holdfast portion;
    a flap limiting layer adjacent to the flap portion, wherein the flap limiting layer and the flap portion form an airflow resistor configured to inhibit exhalation more than inhalation;
    an aligner extending from one side of the flap/holdfast layer and at least partially surrounding the airflow resistor configured to help align the device with a nostril opening; and
    a noise reduction feature configured to minimize noise as air is drawn through the device, wherein the noise-reduction feature comprises projections on the aligner.

14. The device of claim 13, wherein the flap formed in the layer incorporates noise-reduction features in the shape of the flap.

15. A nasal device for inhibiting exhalation more than inhalation, the nasal device comprising:
    a flap/holdfast layer comprising a flap portion and a holdfast portion;
    a flap limiting layer adjacent to the flap portion, wherein the flap limiting layer and the flap portion form an airflow resistor configured to inhibit exhalation more than inhalation;
    an aligner extending from one side of the flap/holdfast layer and at least partially surrounding the airflow resistor configured to help align the device with a nostril opening; and
    a noise reduction feature configured to minimize noise as air is drawn through the device, wherein the noise-reduction feature comprises a thickened region on the flap.

* * * * *